United States Patent
Herrmann et al.

(10) Patent No.: US 8,951,507 B2
(45) Date of Patent: Feb. 10, 2015

(54) FORMULATION WITH IRRITATION REDUCING ACTION COMPRISING BISABOLOL AND [6]-PARADOL

(75) Inventors: Martina Herrmann, Hameln (DE); Oskar Koch, Göttingen (DE); Imke Meyer, Bodenwerder (DE)

(73) Assignee: Symrise AG, Holzminden (DE)

( * ) Notice: Subject to any disclaimer, the term of this patent is extended or adjusted under 35 U.S.C. 154(b) by 84 days.

(21) Appl. No.: 13/500,944

(22) PCT Filed: Oct. 14, 2009

(86) PCT No.: PCT/EP2009/063427
§ 371 (c)(1),
(2), (4) Date: Jun. 19, 2012

(87) PCT Pub. No.: WO2010/000877
PCT Pub. Date: Jan. 7, 2010

(65) Prior Publication Data
US 2012/0258058 A1    Oct. 11, 2012

(51) Int. Cl.
| | |
|---|---|
| A61P 17/00 | (2006.01) |
| A61Q 17/04 | (2006.01) |
| A61Q 19/00 | (2006.01) |
| A61P 39/06 | (2006.01) |
| A61P 31/00 | (2006.01) |
| A61K 31/12 | (2006.01) |
| A61K 8/35 | (2006.01) |
| A61K 8/34 | (2006.01) |
| A61K 31/00 | (2006.01) |
| A61Q 5/00 | (2006.01) |
| A61Q 5/12 | (2006.01) |
| A61Q 9/02 | (2006.01) |
| A61Q 15/00 | (2006.01) |
| A61Q 19/02 | (2006.01) |
| A61Q 11/00 | (2006.01) |

(52) U.S. Cl.
CPC ... A61K 8/34 (2013.01); A61K 8/35 (2013.01); A61K 31/00 (2013.01); A61Q 5/006 (2013.01); A61Q 5/12 (2013.01); A61Q 9/02 (2013.01); A61Q 15/00 (2013.01); A61Q 17/04 (2013.01); A61Q 19/002 (2013.01); A61Q 19/005 (2013.01); A61Q 19/02 (2013.01); A61Q 11/00 (2013.01); A61K 2800/75 (2013.01)
USPC ............................................. 424/59; 514/678

(58) Field of Classification Search
CPC ...... A61K 31/00; A61K 2800/75; A61K 8/34; A61K 8/35; A61Q 5/12; A61Q 19/02; A61Q 17/04; A61Q 19/002; A61Q 19/005; A61Q 11/00; A61Q 15/00; A61Q 9/02
See application file for complete search history.

(56) References Cited

U.S. PATENT DOCUMENTS

| | | | |
|---|---|---|---|
| 2006/0216254 A1* | 9/2006 | Majmudar et al. | ............... 424/62 |
| 2009/0220625 A1 | 9/2009 | Herrmann et al. | |
| 2009/0238905 A1 | 9/2009 | Gurney et al. | |

FOREIGN PATENT DOCUMENTS

| | | | |
|---|---|---|---|
| FR | 2864426 A1 | | 7/2005 |
| JP | 2006036722 A | | 2/2006 |
| WO | WO 2007/042472 | * | 4/2007 |

OTHER PUBLICATIONS

International Search Report and Written Opinion, International Application No. PCT/EP2009/063427, dated Aug. 30, 2010.

* cited by examiner

*Primary Examiner* — David J Blanchard
*Assistant Examiner* — Sarah Chickos
(74) *Attorney, Agent, or Firm* — Dilworth & Barrese, LLP

(57) ABSTRACT

The present invention relates to formulations having an irritation-reducing action, corresponding cosmetic and pharmaceutical products as well as associated methods and uses thereof.

17 Claims, No Drawings

FORMULATION WITH IRRITATION REDUCING ACTION COMPRISING BISABOLOL AND [6]-PARADOL

CROSS REFERENCE TO RELATED APPLICATIONS

This application is a National Phase filing under 35 U.S.C. §371 of International Application No. PCT/EP2009/063427, filed Oct. 14, 2009. The entire contents of each of the above-applications are incorporated herein by reference.

The present invention relates to a formulation having an irritation-reducing action, preferably a skin irritation-reducing action, consisting of or comprising an irritation-reducing amount of [6]-paradol and bisabolol, wherein the weight ratio of [6]-paradol to bisabolol is in the range of from 1:100000 to 1:10, preferably from 1:10000 to 1:20, more preferably from 1:1000 to 1:33. Preferred formulations are described below.

The present invention also relates to a cosmetic product comprising or consisting of a formulation according to the present invention as well as a pharmaceutical product for prophylaxis and/or treatment of irritation, preferably of skin irritation, comprising or consisting of such a formulation.

Moreover the present invention relates to the use of such a formulation for the preparation of a pharmaceutical product for prophylaxis and/or treatment of irritation, preferably of skin irritation, or a cosmetic product.

The present invention also relates to the use of a formulation, a cosmetic product or a pharmaceutical product according to the present invention for prophylaxis and/or treatment of irritation, preferably of skin irritation, and/or for reducing, eliminating or suppressing the irritating action, preferably the skin-irritating action, of a substance or substance mixture.

The present invention also relates to a process for the preparation of a formulation, a cosmetic product or a pharmaceutical product according to the present invention.

The present invention moreover relates to a method for prophylaxis of skin irritation, a method for treatment of skin irritation, a method for reducing, eliminating or suppressing the irritating, preferably the skin-irritating, action of a substance or substance mixture, and a kit comprising (i) a formulation, a cosmetic product or a pharmaceutical product according to the present invention and, spatially separated, (ii) one or more substances or substance mixtures having an irritating, preferably a skin-irritating, action.

In this text, the term "skin" also includes the "mucous membrane" (mucosa), especially the mucous membrane of mouth, throat, gums, nose, respiratory and gastrointestinal tract ("GI tract").

In the cosmetics and pharmaceuticals industry, there is a constant need for agents having an irritation-reducing action.

The mucous membranes, which line various body cavities that are exposed to the external environment and internal organs (e.g. mouth and throat), and the skin in general (in particular the epidermis) are—as barrier organs of the human organism—subjected to external influences to a particular extent. Many intrinsic (e.g. genetic predisposition) and extrinsic (e.g. damage to the skin barrier, action of UV light, irritating or allergy-inducing substances) factors can lead to skin irritation. In connection with this application, "skin irritation" is to be understood as meaning any change to the skin which induces sensorial malaise in humans or animals and/or is characterized by dry, reddened and/or inflamed skin symptoms. The term "sensorial malaise" here of course also includes states such as itching or pain. Skin irritation can include, in particular, phenomenologically different skin states such as: delicate skin, sensitive skin, including sensitive scalp, easily injured skin, atopic skin (atopy), irritated skin or inflamed skin, which may manifest itself in a reddening of the skin, the so-called erythema. Skin irritations can further include irritations of the oral cavity, like periodontitis, gingivitis and the like, as described in more detail below, irritations like rhinosinusitis (common cold), sinusitis, pharyngitis/tonsillitis and the like, as described in more detail below and in US 2009/0238905, incorporated herein by reference, and irritations of the gastrointestinal tract, as described in more detail below and in US 2009/0238905, incorporated herein by reference.

The problem of sensitive skin affects a growing number of adults and children. It is now assumed that up to 50% of the population have a sensitive skin (L. Misery et al., Ann. Dermatol. Venereol. 2005, 132, 425-429). Sensitive skin describes a skin having a reduced irritation threshold for irritants, such as hyper-reactive, intolerant and also atopic skin. In the case of humans with sensitive, delicate or easily injured skin, a phenomenon called "stinging" ("to sting"=becoming injured, burn, be painful) can be observed. Typical adverse phenomena associated with the terms "stinging" or "sensitive skin" are reddening of the skin, tingling, prickling, tautness and burning of the skin and itching. They can be caused by stimulating environmental conditions, such as e.g. massage, action of surfactants, influence of weather, such as heat, cold, dryness and also damp heat, thermal radiation and UV radiation, e.g. from the sun, or psychological stress.

A sensitive scalp is likewise characterized by reddening of the skin, tingling, prickling, burning and itching. Triggers are, for example, soap, shampoos or other hair care compositions, surfactants, hard water having high calcium carbonate concentrations and/or mechanical stress. Erythemas and hyperseborrhoea (excessive production of sebum) of the scalp and dandruff are often associated with the phenomena described.

In approximately 10-20% of the population of industrial countries, with an increasing trend, atopy (atopic syndrome) is to be observed, a hypersensitivity, of familial origin, of the skin (and mucous membranes) to environmental substances with an increased readiness to develop hypersensitivity reactions of the immediate type (allergies) to substances from the natural environment. Atopy is presumed to be of genetic origin. Atopy can manifest itself as atopic dermatitis. In this case, the skin barrier is damaged, the skin is often inflamed and itches.

The erythematous action of the ultraviolet part of sunlight or artificial radiation on the skin is generally known. While rays having a wavelength of less than 290 nm (the so-called UVC range) are absorbed by the ozone layer in the earth's atmosphere, rays in the range between 290 nm and 320 nm, the so-called UVB range, cause erythema, simple sunburn or even more or less severe burns.

Erythematous skin symptoms also occur as concomitant symptoms with certain skin diseases or irregularities. For example, the typical skin rash of the symptoms of acne is regularly reddened to a greater or lesser degree and impairs the well-being of those affected even in mild cases.

Erythemas also occur to an increased extent in the nappy region of infants, and all the more so of babies (nappy dermatitis). Incontinence, a condition which occurs to an increased extent especially in old age, is also often associated with erythemas and reddening of the skin as a consequence of continual exposure to moisture and irritants (incontinence dermatitis).

Periodontitis (as example of an inflammation reaction in the gums or oral mucosa) is an inflammation of the periodontium, i.e. of the tissues that surround and support the teeth. The periodontium comprises various tissues: the gum epithelium (gingival; gums), the connective tissue of the gingiva, the periodontal ligament (desmodontium), the cementum and the surrounding alveolar bone. The desmodontium is located between the surface of the root and the alveolar bone and is a cell-rich connective tissue which holds the tooth in the bony tooth socket, the alveolus. 53 to 74% of the periodontal space is made up of collagen and oxytalan fibre bundles. The portion of the periodontal fibres incorporated into the cementum and the alveolar bone holds the tooth in the alveolus. The main clinical features of periodontitis include inflammation of the gums, attachment loss, formation of periodontal pockets and degradation of the alveolar bone.

The main cause of periodontitis is plaque. This consists of certain components of saliva, food residues and above all bacteria and their decomposition products. This special form of an infectious disease is caused in most cases by *Porphyromonas gingivalis, Bacteroides forsythus* and *Actinobacillus actinomycetemcomitans*. The continuous release of bacterial toxins, especially of lipopolysaccharides (LPS), leads to an unspecific reaction of the immune defense. LPS-stimulated macrophages secrete prostaglandin E2 (PGE2) and proinflammatory mediators, such as interleukins (e.g. IL-1 beta) and TNF-alpha, in the patient's affected tissues. The proinflammatory mediators induce the release of further PGE2 and of matrix-degrading metalloproteinases (matrix metalloproteinases, MMPs) from the resident fibroblasts, which destroy the extracellular matrix of the surrounding connective tissue. This allows bacteria, which initially interacted with the free gingiva, to penetrate further into the underlying connective tissue, continuing inflammation processes there and finally loosening the connection between the uppermost layer of the epithelium and the root of the tooth. A gingival pocket is formed as a consequence. The reaction of the body is the inflammation of the gingiva and the periodontium with damage to the alveolar bone. In the final stage of periodontitis the affected person is at risk of a massive loss of teeth.

Periodontal disease is also widespread in domestic dog and cat populations. Unnatural diets are known to facilitate the buildup of oral microbial communities leading to periodontitis.

Teeth are constructed mainly from a bonelike substance called dentine. In the area of the crown which protrudes from the gum, the dentine is covered with protective enamel. The dental pulp (pulpa; pulpa dentis) is the part in the centre of a tooth made up of living soft to tissue and cells called odontoblasts. It can also be affected by inflammatory processes, caused by caries.

Caries is caused by bacteria in the plaque on the surface of the tooth. Bacteria such as *Streptococcus mutans* and *Lactobacillus casei* convert sugars and food residues into acid, which attacks and destroys tooth enamel and dentine. The continually multiplying, acid-forming plaque bacteria penetrate through holes in the enamel along the canals that pass through the dentine towards the dental pulp (pulpa), leading to inflammation.

In addition to bacteria, chemicals or mechanical damage can also cause irritation or an inflammation reaction in the gums or oral mucosa. Proinflammatory mediators, especially interleukins such as IL-1 alpha and PGE2, are released in this process (Reilly, D. M. and M. R. Green (1999).

The respiratory tract is the part of the anatomy that has to do with the process of respiration. It is divided into 3 segments: the upper respiratory tract, which includes the nose and nasal passages, paranasal sinuses, and throat or pharynx; the respiratory airways, which include the voice box or larynx, trachea, bronchi, and bronchioles; and the lungs, which include the respiratory bronchioles, alveolar ducts, alveolar sacs, and alveoli.

The term upper respiratory infections, commonly referred to as URIs, is used to refer to an acute infection that involves the upper respiratory tract, e.g., the nose, sinuses, pharynx or larynx. In the United States, there are approximately one billion acute upper respiratory illnesses annually.

Acute upper respiratory tract infections include rhinosinusitis (common cold), sinusitis, pharyngitis/tonsillitis, laryngitis and sometimes bronchitis. Symptoms of URIs commonly include congestion, cough, running nose, sore throat, fever, facial pressure and sneezing. Onset of the symptoms usually begins 1-3 days after exposure to a microscopic pathogen, most commonly a virus. The duration of the symptoms is typically 7 to 10 days but may persist longer.

A very common infection is pharyngitis. Pharyngitis is, in most cases, a painful inflammation of the pharynx, and is colloquially referred to as a sore throat. Infection of the tonsils, i.e., tonsillitis, may occur simultaneously. About 90% of cases are caused by viral infection, with the remainder caused by bacterial infection and, in rare cases, oral thrush (fungal candidiasis, e.g., in babies). Some cases of pharyngitis are caused by irritation from environmental irritants such as pollutants or chemical substances.

There are three types of treatment for URIs: symptomatic, remedial and preventive. Symptomatic treatments are aimed at reducing pain and symptoms. Remedial treatments attempt to cure pharyngitis by reducing its spread and speeding up the healing process. Preventive treatments attempt to block the start of an infection.

Remedial treatments are mostly effective for bacterial infections such as streptococcal infections. For viral infections, even with treatment, recovery from pharyngitis generally occurs spontaneously within a few days. Hence the most popular method of treatment is symptomatic. Many preventive treatments are also remedial.

Several non-antibiotic treatments for sore throat have been studied in controlled trials. Analgesics are among the most effective treatment, but there are many simple measures that can also be used.

Symptomatic treatments for URIs include: analgesics that can help reduce the pain associated with a sore throat; throat lozenges and syrups (cough medicine), films strips and chewing gums; mouthwash (when gargled); peppermint candy or other hard candies, gargling, throat sprays and nasal sprays.

The gastrointestinal tract ("GI tract"), also called the digestive tract, the alimentary canal, or the entrails, is the system of organs that receives food, digests the food to extract energy and nutrients, and expels the remaining waste. The major functions of the GI tract are ingestion, digestion, absorption, and excretion.

The upper GI tract consists of the mouth, pharynx, esophagus, and stomach. The mouth contains the buccal mucosa, which contains the openings of the salivary glands; the tongue; and the teeth. Behind the mouth lies the pharynx, which leads to a hollow muscular tube, the esophagus, which connects to the stomach. The stomach, in turn, leads to the small intestine. The lower GI tract comprises the intestines and anus. The intestines include the bowel or intestine, the small intestine, which has three parts: duodenum, jejunum, ileum, the large intestine, which has three parts: cecum with the vermiform appendix attached, the colon (ascending colon, transverse colon, descending colon and sigmoid flexure) and the rectum.

Common inflammations of the gastrointestinal tract include gastro-esophageal reflux diseases, heartburn and peptic ulcers. Physicians first direct treatment to inducing a remission which involves relief of symptoms and healing of the lining of the corresponding membranes and tissues, reducing inflamed tissue and then longer term treatment to maintain the remission.

Remedial and Preventive Treatments: Chamomile is used medicinally against sore stomach, irritable bowel syndrome, and as a gentle sleep aid. It can be taken as an herbal tea, two teaspoons of dried flower per cup of tea. For a sore stomach, some recommend taking a cup every morning without food for two to three months. The primary active ingredient of the essential oil from German Chamomile is bisabolol.

A large number of active compounds having a (skin) irritation-reducing action are indeed already employed in the technical fields referred to, but alternatives nevertheless continue to be sought. In the connection of this text, irritation-reducing action is to be understood as meaning the moderation, reduction, elimination or prevention of irritations, especially of skin irritations, and in particular that of the skin symptoms or skin states described above. The (skin) irritation-reducing action here is based in particular on soothing of the skin, inhibition of inflammation and/or alleviation of reddening.

The object of the present invention was therefore to provide an anti-inflammatory formulation which shows good anti-inflammatory (in particular irritation-reducing) activity, especially on the skin, and, preferably, additionally improved (formulation) properties in cosmetic and/or pharmaceutical products.

A further object of the present invention is to provide corresponding cosmetic and pharmaceutical products as well as a process for the manufacture of such a formulation, such cosmetic and pharmaceutical products.

Further objections underlying the present invention follow from the description below and the present patent claims.

According to the first aspect of the present invention, the underlying object is achieved by a formulation having an irritation-reducing action, preferably a skin irritation-reducing action, consisting of or comprising an irritation-reducing amount of [6]-paradol and bisabolol, wherein the weight ratio of [6]-paradol to bisabolol is in the range of from 1:100000 to 1:10, preferably from 1:10000 to 1:20, more preferably from 1:1000 to 1:33.

It is particularly preferred, when the amounts of [6]-paradol and bisabolol in the formulation are adjusted such that the irritation-reducing action of [6]-paradol and bisabolol is increased synergistically.

In the search for alternative irritation-reducing agents, however, it should be noted that the substances used should be toxicologically acceptable, tolerated well by the skin and stable or easily stabilized by common means (in particular in conventional cosmetic and/or pharmaceutical formulations), should have the lowest possible intrinsic odour and the lowest possible intrinsic colour. In addition, they should be inexpensive to prepare.

The skin irritation-reducing action of bisabolol is already described in the prior art (e.g. H. Schilcher, Die Kamille: Handbuch für Ärzte, Apotheker u. a. Naturwissenschaftler [Camomile: Handbook for Doctors, Pharmacists and Other Scientists], Wissenschaftliche Verlagsgesellschaft, Stuttgart, 1987). However, there was no indication hitherto that mixtures of bisabolol with [6]-paradol, in particular formulations as described above, have, compared with the components used individually, a significantly improved, synergistic, irritation-reducing action, especially a skin irritation-reducing action. In the connection of this text, synergistic action is to be understood as meaning an action which is increased beyond the additive action of the compounds displaying synergy. This can be recorded by the synergy index (SI) value according to Kull (D. C. Steinberg, Cosmetics & Toiletries 2000, 115 (11), 59-62 and F. C. Kull et al., Applied Microbiology 1961, 9, 538-541) (see also below, example 3, table 4). Substance combinations in which both components display the synergistically increased action, and also substance combinations in which only one component displays the synergistically increased action, while the other component acts merely as an intensifier (booster), fall under the given definition of the synergy effect. In the present case it was observed that bisabolol and [6]-paradol display a synergistically increased action. A synergistic combination of active compounds has the advantage that overall less active compound is required to achieve the particular action.

[6]-Paradol is a known substance [IUPAC-Name: 1-(4-hydroxy-3-methoxyphenyl)-decan-3-one, CAS number: 27113-22-0] having the following formula:

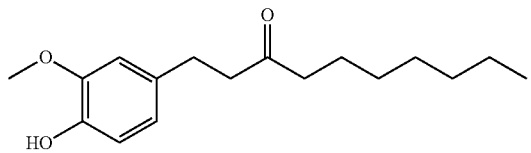 [SMILES: CCCCCCCC(=O)CCc1ccc(O)c(OC)c1]

In Bioorg. Chem. 2001, 29, 156-163, the investigation of several ginger constituents was to reported. There, the inhibition of cyclooxygenase-2 (COX-2) enzyme activity in the intact cell was evaluated. Activation of COX results in the synthesis of a wide spectrum of prostaglandins, which are known to be important mediators in inflammatory processes. It was reported that ginger constituents [10]-gingerol, [6]-shogaol, [8]-shogaol and [8]-paradol showed the greatest inhibitory activity, i.e. the smallest $IC_{50}$-values, towards COX-2, while [6]-paradol (corresponding to compound 7 in said publication) showed the second-lowest activity (i.e. the second-highest $IC_{50}$-value) of the ginger constituents examined in Bioorg. Chem. 2001, 29, 156-163.

However, in own experiments, [6]-paradol unexpectedly showed a relatively strong inhibitory activity towards prostaglandin $E_2$ ($PGE_2$), an important inflammatory mediator in the skin (see below, example 2). From the compounds tested ([6]-paradol, [6]-gingerol, [8]-gingerol and [8]-paradol) [6]-paradol showed the highest activity, i.e. the lowest $IC_{50}$-value, towards $PGE_2$.

In view of the above prior art relating to the COX-2 inhibitory activity and prior to our own experiments relating to the $PGE_2$ inhibitory activity of, inter alia, [6]-paradol, it was particularly surprising that [6]-Paradol in combination with bisabolol (as described above) provides a strong, synergistically increased irritation-reducing activity.

For Australian-grown ginger (Zingiber officinale), the co-occurrence of bisabolol and [6]-paradol in carbon dioxide extracts obtained by supercritical fluid extraction is described (J. P. Bartley and P. Foley, J. Sci. Food Agric. 1994, 66, 365-371 and J. P. Bartley and A. L. Jacobs, J. Sci. Food Agric. 2000, 80, 209-215). According to GC quantification, both are minor constituents and the ratio of bisabolol to [6]-paradol in the obtained extracts ranges from 1.8:1 to 1:2.4. However as GC quantification only gives values for volatile, GC compatible substances, the absolute contents of bisabolol and [6]-paradol in the carbondioxide extracts is not deducible from this document.

WO 2007/042472 A1 discloses synergistic mixtures of bisabolol and ginger extract or compounds obtainable from a separation of a ginger extract which are chosen from the group consisting of gingerols, shogaols, gingerdiols, dehydrogingerdiones, paradols and derivatives thereof. [6]-Paradol is not mentioned in WO 2007/042472 A1. In addition, [6]-paradol only occurs in trace amounts in ginger oleoresin (D. W. Connell, Aust. J. Chem. 1970, 23, 369-376). In own experiments we could not detect via HPCL-MS any [6]-paradol from ginger extract as obtained according to WO 2007/042472 A1, i.e. such extracts contain a maximum amount of [6]-paradol of less than 10 ppm, if any.

Again, it was thus neither from these nor from further publications foreseeable that [6]-paradol in combination with bisabolol exhibits particularly good anti-inflammatory activity and synergistically increased irritation-reducing action. It was particularly surprising that a formulation according to the present invention shows a highly synergistic irritation-reducing activity. Additionally, e.g. on skin irritated by a detergent, such a formulation is significantly superior to individually dosed bisabolol or [6]-paradol.

In contrast to ginger extracts, e.g. as described in WO 2007/042472 A1, which generally are of yellow colour, [6]-paradol is advantageously colourless, in particular if it is of synthetic origin. This property makes [6]-paradol particularly suitable for use in cosmetic compositions or products as these are preferably white or colourless.

Furthermore, in contrast to gingerols and shogaols, in particular to gingerols, which are labile and prone to degradation (J. Pharm. Sci. 2001, 1658-1664), thus showing insufficient stability, according to own experiments [6]-paradol is very stable in cosmetic compositions or products, even at varying pH-values, i.e. in basic, neutral or acidic cosmetic compositions or products.

From a toxicological point of view, [6]-paradol is also advantageous, as it is not mutagenic (Environmental Mutagens and Carcinogens 1998, 18(1), 32-36), in contrast to certain other constituents occurring in ginger extract, e.g. [6]-gingerol, which is reported to be a potent mutagen (Mutat Res. 1982, 103(2), 119-26).

A formulation according to the present invention that further comprises [6]-gingerol is preferably a formulation as described above, wherein the weight ratio of [6]-paradol to [6]-gingerol is greater than 10:1, preferably greater than 100:1, more preferably greater than 1000:1 and even more preferably greater than 10000:1.

Taking the above aspects into account, particularly preferred formulations, cosmetic products and pharmaceutical products (see below) according to the present invention are preferably free of [6]-gingerol, preferably free of gingerols and/or shogaols, particularly free of gingerols, more preferably free of gingerols and shogaols, and, optionally, free of gingerdiols and/or dehydrogingerdiones and/or zingerone. Most preferably they are free of gingerols, shogaols, gingerdiols, dehydrogingerdiones and zingerone.

Therefore, a formulation according to the present invention is preferably
  free of [6]-gingerol,
  preferably free of gingerols,
  more preferably free of gingerols and shogaols,
  more preferably free of gingerols, shogaols, gingerdiols, dehydrogingerdiones and zingerone.
Also preferred is a formulation according to the present invention (as described above),
  wherein the formulation is free of substance mixtures obtainable from an extract of ginger, preferably free of substance mixtures obtainable from a separation of ginger extract comprising a compound which is chosen from the group consisting of gingerols, shogaols, gingerdiols, dehydrogingerdiones and paradols. Accordingly, a formulation according to the present invention preferably does not consist of or comprise a ginger extract.

The synergistic combinations of bisabolol and [6]-paradol, i.e. the formulations according to the present invention, are preferably colourless, are advantageously of low odour and show good stability even at pH values 7, which is of particular interest for several cosmetic products such as sunscreen formulations, soaps, deo sticks, alkaline hair colourations and oral care formulations like tooth pastes. The synergistic combinations of bisabolol and [6]-paradol are advantageously stable over a wide range of pH-values, generally in cosmetic compositions or products having a pH-value in the range of 4 to 10, in particular in cosmetic compositions or products having a pH-value in the range of 5 to 9. The stability of the synergistic combinations of bisabolol and [6]-paradol refers to both chemical and colour stability: it was found that, if any, only slight chemical degradation and, if any, only slight discolouration occurs at the pH-values indicated above.

It has also been found that the synergistic irritation-reducing activity of formulations to according to the invention is not limited solely to acceleration of the subsidence ("repair") of the inflammation and/or reddening of the skin compared with untreated skin. Rather, the formulation according to the invention also has advantageously a highly synergistic action in reducing the development of erythema ("protection") e.g. due to detergents, UV irradiation or another of the abovementioned factors.

On the basis of the particularly significant increase in the ((skin) irritation-reducing) action of bisabolol and [6]-paradol, the formulation according to the invention is particularly suitable for reducing skin irritation, in particular for soothing the skin and/or inhibiting inflammation and/or reducing reddening, even at a low dosage of the formulation according to the invention. Corresponding uses and methods according to the present invention are described further below.

Also preferred is a formulation according to the present invention (as described above), wherein the total amount of [6]-paradol is at least 10 ppm, preferably at least 100 ppm, more preferably at least 1000 ppm, based on the total weight of the formulation.

Particularly preferred for the objects of the present invention is a formulation according to the present invention (as described above), wherein
  the total amount of [6]-paradol is in the range of from 0.001 to 10 wt. %, preferably from 0.01 to 5 wt. %, more preferably from 0.1 to 3 wt. %, and/or
  the total amount of bisabolol is in the range of from 99.999 to 90 wt. %, preferably from 99.99 to 95 wt. %, more preferably from 99.9 to 97 wt. %,
based on the total weight of the formulation, in particular of a formulation in terms of a crude (raw) product.

According to one aspect of the present invention the formulation according to the invention (as described above) is preferably a cosmetic formulation. A cosmetic formulation is preferably a ready-to-use formulation, i.e. a cosmetic product, or may be used as ingredient for a cosmetic product (see below). In the context of this text, "ready-to-use" is to be understood as meaning that the (cosmetic) formulation is intended for coming into contact with the skin in an unchanged form.

The total amount of bisabolol and [6]-paradol together in (ready-to-use) cosmetic formulations according to the invention is preferably in the range of from 0.001 to 5 wt. %, preferably in the range of from 0.01 to 1 wt. %, more preferably in the range of from 0.01 to 0.25 wt. %, based on the total weight of the formulation.

In summary, particularly preferred are formulations according to the present invention, wherein
(a) the weight ratio of [6]-paradol to bisabolol is in the range of from 1:100000 to 1:10, preferably from 1:10000 to 1:20, more preferably from 1:1000 to 1:33 and/or
(b) the total amount of [6]-paradol is in the range of from 0.001 to 10 wt. %, preferably from 0.01 to 5 wt. %, more preferably from 0.1 to 3 wt. % and/or
the total amount of bisabolol is in the range of from 99.999 to 90 wt. %, preferably from 99.99 to 95 wt. %, more preferably from 99.9 to 97 wt. %, and/or
(c) the total amount of [6]-paradol and bisabolol is in the range of from 0.001 to 5 wt. %, preferably from 0.01 to 1 wt. %, more preferably from 0.01 to 0.25 wt. %, based on the total weight of the formulation.

In view of the upper and lower limits according to (a), (b) and (c) as described above, it has to be noted that not all of the aforementioned weight ratios and total amounts of bisabolol and [6]-paradol can be combined with each other at the same time. Depending on different desired properties of the formulation, different limits may be advantageous.

According to a further aspect of the present invention the bisabolol contained in a formulation according to the present invention (as described above) is preferably synthetic bisabolol, in particular for cosmetic skin care applications.

According to a further aspect of the present invention the bisabolol contained in a formulation according to the present invention (as described above) is preferably natural bisabolol, in particular for oral care and foodstuffs.

However, the bisabolol used in the context of the present invention can principally be of natural or synthetic origin, and is preferably "alpha-bisabolol". The term "alpha-bisabolol" here includes (+)-alpha-bisabolol, (−)-alpha-bisabolol, (+)-epi-alpha-bisabolol and (−)-epi-alpha-bisabolol as well as mixtures of two, three or all of the isomers of alpha-bisabolol mentioned. In particular, the term "alpha-bisabolol" includes racemic mixtures of (+/−)-alpha-bisabolol and/or (+/−)-epi-alpha-bisabolol. Preferably, the bisabolol used is synthetically prepared or natural (−)-alpha-bisabolol and/or synthetic mixed-isomer alpha-bisabolol. If natural (−)-alpha-bisabolol is used, this can also be employed as a constituent of an essential oil or of a plant extract or of a fraction thereof, for example as a constituent of (fractions of) oil or extracts of camomile or of Vanillosmopsis (in particular Vanillosmopsis erythropappa or Vanillosmopsis arborea). Synthetic alpha-bisabolol is obtainable, for example, under the name "Dragosantol" or "Dragosantol 100" from Symrise.

The [6]-paradol used in the present invention can also be of natural or synthetic origin. If natural [6]-paradol is used, it can be employed as a constituent of a plant extract or of a fraction thereof, for example as a constituent of (fractions of) extracts of Aframomum melegueta, also known as grains of paradise. Extracts or fractions thereof according to the present invention contain at least 15 wt.-% [6]-paradol. As extracts and fractions thereof often contain colouring and/or smelling constituents, it is preferred to use highly pure natural [6]-paradol. For the separation of a grains of paradise extract for the preparation of [6]-paradol, it is not difficult for the person skilled in the art to choose suitable separation methods known from the prior art. Synthetic [6]-paradol can be obtained by condensation of vanillin with 2-nonanone using 1.5 mol-equivalents of potassium hydroxide in methanol. The resulting alpha,beta-unsaturated aromatic ketone is reduced by hydrogenation under catalysis of Raney-Nickel at moderate conditions. Other catalysts (Pd/C) are unfavoured, because they may lead to overhydrogenation resulting in the corresponding alcohol of [6]-paradol. Most preferably, synthetically prepared [6]-paradol is used for the objects of the present invention.

The present invention also provides a formulation as described above, in particular a formulation characterized herein before as preferred, for use as a medicament, preferably for use as a medicament for prophylaxis or treatment of (skin) irritation.

Therefore the present invention also relates to the use of a formulation according to the to present invention for the preparation of a medicament for prophylaxis or treatment of (skin) irritation.

The present invention also relates to a formulation as described above for use in a method for prophylaxis or treatment of skin irritation, in particular in a method for reducing the release of series-2 prostaglandins in human or animal cells, in particular in a method for reducing the release of Prostaglandin $E_2$ in human or animal cells.

A further aspect of the present invention relates to a pharmaceutical product (medicament), preferably a dermatological product, for prophylaxis and/or treatment of irritation, preferably of skin irritation, comprising or consisting of a formulation according to the invention (as described above).

Such a pharmaceutical product can be employed in the field of human and veterinary medicine against a large number of diseases, such as, for example, urticaria, contact dermatitis, atopy and generally all inflammation processes, included tooth and gum inflammations, such as parodontosis, mouth or throat inflammations, such as sore throat and irritations of the respiratory or gastrointestinal tract linings and tissues.

Another aspect of the present invention relates to a cosmetic product comprising or consisting of a formulation according to the invention, preferably a cosmetic formulation (as described above).

A formulation according to the invention can be further processed to a solid form (preferably a cosmetic or pharmaceutical product) by optionally adding a pharmaceutically acceptable solid carrier to the formulation and then drying the mixture by suitable processes. In this context, such a solid which is at least not toxic to the organisms on which it is to be used is pharmaceutically and/or cosmetically acceptable.

The formulation according to the invention can also be further processed to a dilution in liquid form (preferably a cosmetic or pharmaceutical product) by optionally adding a pharmaceutically and/or cosmetically acceptable solvent, such as e.g. neutral oil, mineral oil, silicone oil, plant oils, fatty alcohols, fatty acid esters, ethanol, 1,2-propylene glycol, 1,3-butylene glycol, glycerol, 1,2-pentanediol and water or mixtures of two or more of the solvents mentioned. Such formulations or products are further processable in particular for cosmetic purposes. Further optional components of described formulations or (cosmetic or pharmaceutical) products are for example solubilizing agents, preservatives and antioxidants.

The formulation according to the invention or, in particular, the liquid or solid form described above comprising the formulation, can furthermore be processed by encapsulation. Here, the formulation according to the invention or, in particular, the liquid or solid form comprising the formulation, is encapsulated with a solid shell material, which is preferably chosen from starches, degraded or chemically or physically modified starches (in particular dextrins and maltodextrins), gelatines, wax materials, liposomes, gum arabic, agar-agar, ghatti gum, gellan gum, modified and non-modified celluloses, pullulan, curdlan, carrageenans, algic acid, alginates, pectin, inulin, xanthan gum and mixtures of two or more of the substances mentioned.

The solid shell material is preferably selected from gelatine (pork, beef, poultry and/or fish gelatines or mixtures thereof, preferably including at least one gelatine having a Bloom value of greater than or equal to 200, preferably having a Bloom value of greater than or equal to 240), maltodextrin (preferably obtained from maize, wheat, tapioca or potato, preferred maltodextrins displaying a DE value in the range from 10 to 20), modified cellulose (e.g. cellulose ether), alginates (e.g. Na alginate), carrageenan (beta-, iota-, lambda- and/or kappa-carrageenan), gum arabic, curdlan and/or agar-agar. Gelatine is used in particular because of its good availability in various Bloom values. Particularly preferred for oral hygiene purposes are seamless gelatine or alginate capsules, whose shell dissolve very quickly in the mouth or bursts when chewed, thus releasing the active ingredient in the oral cavity. Production can take place as described for example in EP 0 389 700 A, JP 7 196 478, U.S. Pat. Nos. 4,251,195, 6,214,376, WO 03/055587 or WO 2004/050069.

Essential fields of use for formulations according to the invention are cosmetic or pharmaceutical, in particular dermatological, formulations or products (see above), which have—apart from the presence of the synergistic formulation according to the invention—the conventional composition of cosmetic or pharmaceutical formulations or products and serve for treatment, care and/or cleansing of the skin and/or hair or as a make-up product in decorative cosmetics, in particular as products for dermatological light protection. Preferred formulations or products according to the invention can accordingly be present in or as a cleansing composition, e.g. soap, syndet, liquid washing, shower and bath preparation, skin care composition, e.g. emulsion (as a solution, dispersion, suspension; to cream, lotion or milk of the W/O, O/W or multiple emulsion, PIT emulsion, emulsion foam, micro-, nanoemulsion, Pickering emulsion type, depending on the preparation process and constituents), ointment, paste, gel (including hydro-, hydrodispersion-, oleogel), alcoholic or aqueous/alcoholic solution, oil, toner, balsam, serum, powder, wipe, Eau de Toilette, Eau de Cologne, perfume, wax, including the presentation form as a stick, roll-on, (pump) spray, aerosol (foaming, non-foaming or after-foaming), skin care composition as a foot care composition (including keratolytics, deodorant), as an insect repellent composition, as a sunscreen composition, as a self-tanning composition and/or aftersun preparation, skin care composition as a shaving composition or after-shave, as a hair-removing composition, as a hair care composition, such as e.g. shampoo (including shampoo for normal hair, for greasy hair, for dry, stressed (damaged) hair, 2-in-1 shampoo, anti-dandruff shampoo, baby shampoo, shampoo for a dry scalp, shampoo concentrate), conditioner, hair treatment cure, hair tonic, hair lotion, hair rinse, styling cream, pomade, permanent wave and fixing compositions, hair smoothing composition (straightening composition, relaxer), hair setting composition, styling aid (e.g. gel or wax); blonding composition, hair colouring composition, such as e.g. temporary, directly absorbed, semi-permanent hair colouring composition, permanent hair colouring composition), skin care composition as a decorative body care composition, such as e.g. nail care composition (nail varnish and nail varnish remover), decorative cosmetic (e.g. powder, eye shadow, kajal pencil, lipstick), make-up, make-up remover, skin care composition as a deodorant and/or antiperspirant.

A further aspect of the present invention relates to products according to the invention in the form of oral care products (oral hygiene products), wherein the oral care product is preferably in the form of toothpaste, dental cream, dental gel, dental powder, tooth-cleaning liquid, tooth-cleaning foam, mouthwash, dental cream and mouthwash as a 2-in-1 product, sugar-free candies for sucking, oral spray, dental floss or dental care chewing gum. The activity of the formulations according to the invention contained in such products also manifests itself remarkably well in the field of oral hygiene.

A further aspect of the present invention relates to products according to the invention in the form of products with irritation-reducing action on the throat, the respiratory tract and the gastrointestinal tract, wherein the throat care product is preferably in the form of lozenge, sweet for sucking or chewing such as hard candy, candy, fruit gum or chewing gum, the products with irritation-reducing action on the respiratory tract is preferably a cough medicine with antitussives or expectorants (cough drops, lozenges or syrups) or a nasal spray and the products with irritation-reducing action on the gastrointestinal tract is preferably a stomach remedy (antacid).

Formulations according to the present invention can advantageously be combined, in particular in cosmetic products, with further conventional components, such as, for example:
preservatives, in particular those described in US 2006/0089413, antimicrobial agents, such as e.g. antibacterial agents or agents to treat yeast and mold, in particular those described in WO 2005/123101, antiacne and sebum reducing agents, in particular those described in WO 2008/046791, compounds against ageing of the skin, in particular those described in WO 2005/123101, antidandruff agents, in particular those described in WO 2008/046795, antiirritants (antiinflammatory agents, irritation-preventing agents, irritation-inhibiting agents), in particular those described in WO 2007/042472 and US 2006/0089413, antioxidants, in particular those described in WO 2005/123101, carrier materials, in particular those described in WO 2005/123101, chelating agents, in particular those described in WO 2005/123101, deodorizing agents and antiperspirants, in particular those described in WO 2005/123101, moisture regulators (moisture-donating agents, moisturizing substance, moisture-retaining substances), in particular those described in WO 2005/123101, osmolytes, in particular those described in WO 2005/123101, compatible solutes, in particular those described in WO 01/76572 and WO 02/15868, proteins and protein hydrolysates, in particular those described in WO 2005/123101, skin-lightening agents, in particular those described in WO 2007/110415, skin-tanning agents, in particular those described in WO 2006/045760, cooling agents, in particular those described in WO 2005/123101, skin-cooling agents, in particular those described in WO 2005/123101, warming agents, in particular those described in WO 2005/123101, UV-absorbing agents, in particular those described in WO 2005/123101, UV filters, in particular those described in WO 2005/123101, benzylidene-beta-dicarbonyl compounds in accordance with WO 2005/107692 and alpha-benzoyl-cinnamic acid nitriles in accordance with WO 2006/015954, insect repellents, in particular those described in WO 2005/123101, plant parts, plant extracts, in particular those described in WO 2005/123101, vitamins, in particular those described in WO 2005/123101, emulsifiers, in particular those described in WO 2005/123101, gelling agents, in particular those described in WO 2005/123101, oils in particular those described in WO 2005/123101, waxes in particular those described in WO 2005/123101, fats in particular those described in WO 2005/123101, phospholipids, in particular those described in WO 2005/123101, saturated fatty acids and mono- or polyunsaturated fatty acids and alpha-hydroxy acids and polyhydroxy-fatty acids and esters of saturated and/or unsaturated branched and/or unbranched alkane carboxylic acids, in particular those described in WO 2005/123101, surface-active substances (surfactants) in particular those described in WO 2005/123101, skin repair agents comprising cholesterol and/or fatty acids and/or ceramides and/or pseudoceramides, in particular those described in WO 2006/053912, dyestuffs and colourants and pigments, in particular those described in WO 2005/123101, aroma chemicals and flavors and fragrances, in particular those described in S. Arctander, Perfume and Flavor Chemicals, private publishing house, Montclair, N.J., 1969 and Surburg, Panten, Common Fragrance and Flavor Materials, 5th Edition, Wiley-VCH, Weinheim 2006, preferably those explicitly mentioned in US 2008/0070825, alcohols and polyols, in particular those described in WO 2005/123101, organic solvents, in particular those described in WO 2005/123101, silicones and silicone oils and silicone derivatives, virucides, abrasives, anti-cellulite agents, astringents, antiseptic agents, antistatics, binders, buffers, cell stimulants, cleansing agents, care agents, depilatory agents, softeners, enzymes, essential oils, in particular those described in US 2008/0070825, fibres, film-forming agents, fixatives, foam-forming agents, foam stabilizers, substances for preventing foaming, foam boosters, gel-forming agents, hair growth activators, hair growth inhibitors, hair care agents, hair-setting agents, hair-straightening agents, hair-smoothening, bleaching agents, strengthening agents, stain-removing agents, optically brightening agents, impregnating agents, dirt-repellent agents, friction-reducing agents, lubricants, opacifying agents, plasticizing agents, covering agents, polish, gloss agents, polymers, powders, peptides, mono-, di- and oligosaccharides, re-oiling agents, abrading agents, skin-soothing agents, skin-cleansing agents, skin care agents, skin-healing agents, skin-protecting agents, skin-softening agents, skin-smoothing agents, nourishing agents, skin-warming agents, stabilizers, detergents, fabric conditioning agents, suspending agents, thickeners, yeast extracts, algae or microalgae extracts, animal extracts, liquefiers, colour-protecting agents, anticorrosives and electrolytes.

Formulations and products according to the invention can contain one or more further anti-irritant agents. A more rapid reduction of irritation based in part on further synergistic effects can be achieved in this way.

Anti-irritant agents are for example steroidal anti-inflammatory substances of the corticosteroid type, such as e.g. hydrocortisone, hydrocortisone derivatives, such as hydrocortisone 17-butyrate, dexamethasone, dexamethasone phosphate, methylprednisolone or cortisone; non-steroidal anti-inflammatories like oxicams, such as piroxicam or tenoxicam; salicylates, such as aspirin, Disalcid, Solprin or fendosal; acetic acid derivatives, such as diclofenac, fenclofenac, indomethacin, sulindac, tolmetin or clindanac; fenamates, such as mefenamic, meclofenamic, flufenamic or niflumic; propionic acid derivatives, such as ibuprofen, naproxen or benoxaprofen, or pyrazoles, such as phenylbutazone, oxyphenylbutazone, febrazone or azapropazone. Alternatively, natural anti-inflammatory substances or reddening- and/or itching-alleviating substances can be employed. Plant extracts, specific highly active plant extract fractions and highly pure active substances isolated from plant extracts, can be employed like extracts, fractions and active substances from aloe vera, *Commiphora* species, *Rubia* species, *Rubus* species, willow, rose-bay, willowherb, oats, calendula, arnica, St. John's wort, honeysuckle, rosemary, sage, melissa, Passiflora incarnata, Sophora japonica, witch hazel, Pueraria, Dianthus or Echinacea, as well as pure substances, such as, inter alia, apigenin, apigenin-7-glucoside, rosmarinic acid, boswellic acid, phytosterols, glycyrrhizic acid, glabridin, licochalcone A and anthranilic acid amides, such as, in particular, avenanthramides or dianthramides, are particularly preferred.

The total amount of anti-irritants, including [6]-paradol and bisabolol, in a formulation or product according to the invention is preferably in the range of from 0.0001 to 20 wt. %, preferably from 0.0001 to 10 wt. %, in particular from 0.001 to 5 wt. %, based on the total weight of the formulation or product, respectively.

The synergistic combinations consisting of bisabolol and [6]-paradol are stable with respect to chemical and colour stability. In some cosmetic formulations and products, in particular those having a high water content (60 wt.-% or more, based on the total weight of the composition or product), some chemical degradation and/or some discolouration may occur, in particular when said formulation and product is exposed to light over a prolonged period of time. To improve the stability of such formulations and products it is advantageous to include one or more (colour) stabilizers into a formulation or product according to the invention, in particular for formulation or products having a water content of 60 wt.-% or more, based on the total weight of the formulation or product.

Therefore, in a preferred embodiment formulations and products according to the invention preferably contain one or more antioxidants (preferably selected from those listed below), UV-filters (preferably selected from those listed below), inorganic pigments (preferably selected from those described in WO 2005/123101), (metal) chelators (preferably selected from those listed below), photostabilizers, triplet-triplet quenchers, excited state quenchers, singlet oxygen quenchers such as for example diethylhexyl syringylidene malonate (obtainable, for example, under the name "Oxynex ST liquid" from Merck), benzotriazolyl dodecyl p-cresol (obtainable, for example, under the name "Tinogard TL" from Ciba), sodium benzotriazolyl butylphenol sulfonate (obtainable, for example, under the name "Tinogard TS" from Ciba), tris(tetramethylhydroxypiperidinol) citrate (obtainable, for example, under the name "Tinogard QS" from Ciba), octadecyl di-t-butyl-4-hydroxyhydrocinnamate (obtainable, for example, under the name "Tinogard TS" from Ciba), pentaerythrityl tetra-di-t-butyl hydroxyhydrocinnamate (obtainable, for example, under the name "Tinogard TT" from Ciba), benzophenone-4 (obtainable, for example, under the name "Uvinul 40 MS" from BASF) or diethylhexyl 2,6-naphthalate (obtainable, for example, under the name "Corapan TO" from Symrise).

Formulations or products according to the present invention in the form of cosmetic or dermatologically active formulations or products are preferably applied to the skin and/or hair in a sufficient amount in the conventional manner for cosmetics or dermatics. In this context, cosmetic or dermatological formulations or products according to the present invention which additionally act as sunscreen compositions offer particular advantages. These formulations or products advantageously comprise at least one UVA filter and/or at least one UVB filter and/or at least one inorganic pigment. In this context, the formulations or products can be in various forms such as conventionally employed for sunscreen formulations, e.g. in the form of a solution, an emulsion of the water-in-oil (W/O) type or of the oil-in-water (O/W) type or a multiple emulsion, for example of the water-in-oil-in-water (W/O/W) type, a gel, a hydrodispersion, a solid stick or also an aerosol.

Therefore, the present invention preferably relates to a formulation, a cosmetic product or a pharmaceutical product as described above, further comprising one or more UV filter substances, in particular
- one or more organic UVA filter substances and/or
- one or more organic UVB filter substances and/or
- one or more organic UVA and UVB filter substances and/or
- one or more inorganic UV filter substances (inorganic pigments).

Thus, formulations or products according to the present invention can advantageously be combined with substances which absorb UV radiation. In order to provide formulations or products which (additionally) protect the hair or skin from ultraviolet radiation, the total amount of filter substances contained in the formulation or product according to the present invention is preferably in the range of from 0.01 to 40 wt.-%, preferably from 0.1 to 10 wt.-%, in particular from 1.0 to 5.0 wt.-%, based on the total weight of the formulation or product.

Particularly preferred formulations or products are sunscreen formulations in the form of aqueous emulsions, preferably of the water-in-oil (W/O) or of the oil-in-water (O/W) type or a multiple emulsion, for example of the water-in-oil-in-water (W/O/W) type, more preferably of the oil-in-water (O/W) type.

Preferred sunscreen formulations of the present invention comprise a total amount of organic UV filters of more than 10 wt.-%, preferably a total amount in the range of from 12 to 40 wt.-%, more preferred in the range of from 15 to 35 wt.-%, based on the total weight of the sunscreen formulation.

In this context advantageous organic UV filters are preferably selected from the group consisting of:
p-aminobenzoic acid
p-aminobenzoic acid ethyl ester (25 mol) ethoxylated
p-dimethylaminobenzoic acid-2-ethylhexyl ester
p-aminobenzoic acid ethyl ester (2 mol) N-propoxylated
p-aminobenzoic acid glycerol ester
salicylic acid homomethyl ester (homosalates) (Neo Heliopan HMS)
salicylic acid-2-ethylhexyl ester (Neo Heliopan®OS)
triethanolamine salicylate
4-isopropyl benzyl salicylate
anthranilic acid menthyl ester (Neo Heliopan®MA)
diisopropyl cinnamic acid ethyl ester
p-methoxycinnamic acid-2-ethylhexyl ester (Neo Heliopan® AV)
diisopropyl cinnamic acid methyl ester
p-methoxycinnamic acid isoamyl ester (Neo Heliopan®E 1000)
p-methoxycinnamic acid diethanolamine salt
p-methoxycinnamic acid isopropyl ester
2-ethylhexyl-2-cyano-3,3-diphenyl acrylate (Neo Heliopan®303)
ethyl-2-cyano-3,3'-diphenyl acrylate
2-phenylbenzimidazole sulfonic acid and salts (Neo Heliopan®Hydro)
3-(4'-trimethylammonium) benzylidene bornan-2-one methyl sulfate
terephthalylidene dibornane sulfonic acid and salts (Mexoryl®SX)
4-t-butyl-4'-methoxydibenzoyl methane (avobenzone)/(Neo Heliopan®357)
beta-imidazole-4(5)-acrylic acid (urocanic acid)
2-hydroxy-4-methoxybenzophenone (Neo Heliopan®BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
3-(4'-sulfo)benzylidene bornan-2-one and salts
3-(4'-methyl benzylidene)-d,l-camphor (Neo Heliopan®MBC)
3-benzylidene-d,l-camphor
4-isopropyl dibenzoyl methane
2,4,6-trianilino-(p-carbo-2'-ethylhexyl-1'-oxy)-1,3,5-triazine
phenylene bis-benzimidazyl tetrasulfonic acid disodium salt (Neo Heliopan®AP)
2,2'-(1,4-phenylene)-bis-(1H-benzimidazole-4,6-disulfonic acid), monosodium salt
N-[(2 and 4)-[2-(oxoborn-3-ylidene)methyl]benzyl]acrylamide polymer
2-(2H-benzotriazol-2-yl)-4-methyl-6-(2-methyl-3(1,3,3,3-tetramethyl-1-(trimethylsilyl)oxy)disiloxyanyl)propyl) phenol (Mexoryl®XL)
4,4'-[(6-[4-(1,1-dimethyl)aminocarbonyl)phenylamino]-1-1,3,5-triazine-2,4-diyl)diimino]-bis-(benzoic acid-2-ethylhexyl ester) (Uvasorb®HEB)
2,2'-methylene bis-(6-(2H-benzotriazol-2-yl)-4-1,1,3,3-tetramethylbutyl)phenol), (Tinosorb®M)
2,4-bis-[4-(2-ethylhexyloxy)-2-hydroxyphenyl]-1,3,5-triazine
benzylidene malonate polysiloxane (Parsol SLX)
glyceryl ethylhexanoate dimethoxycinnamate
disodium-2,2'-dihydroxy-4,4'-dimethoxy-5,5'-disulfobenzophenone
dipropylene glycol salicylate
sodium hydroxymethoxybenzophenone sulfonate
4,4',4-(1,3,5-triazine-2,4,6-triyltriimino)-tris-benzoic acid tris(2-ethylhexyl ester) (Uvinurl®T150)
2,4-bis-[{(4-(2-ethylhexyloxy)-2-hydroxy}phenyl]-6-(4-methoxyphenyl)-1,3,5-triazine (Tinosorb®S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-[4-(2-methoxyethylcarbonyl)phenylamino]-1,3,5-triazine
2,4-bis-[{4-(3-(2-propyloxy)-2-hydroxypropyloxy)-2-hydroxy}phenyl]-6-[4-(2-ethylcarboxyl) phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2"-methylpropenyloxy)-2-hydroxy}phenyl]-6-(4-methoxyphenyl)-1,3,5-triazine
2,4-bis-[{4-(1',1',1',3'5',5',5'-heptamethylsiloxy-2"-methylpropyloxy)-2-hydroxy}phenyl]-6-(4-methoxyphenyl)-1,3,5-triazine
2-(4-diethylamino-2-hydroxybenzoyl) benzoic acid hexyl ester (Uvinul® A Plus)
indanylidene compounds according to DE 100 55 940 (WO 02/38537)

Organic UV filters which are particularly preferred in formulations and products of the present invention (in particular if they are in the form of a sunscreen formulation), particularly in preferred amounts as mentioned above, are:
p-aminobenzoic acid
3-(4'-trimethylammonium) benzylidene bornan-2-one methyl sulfate
salicylic acid homomethyl ester (Neo Heliopan®HMS)
2-hydroxy-4-methoxybenzophenone (Neo Heliopan®BB)
2-phenylbenzimidazole sulfonic acid (Neo Heliopan®Hydro)
terephthalylidene dibornane sulfonic acid and salts (Mexoryl®SX)
4-tert-butyl-4'-methoxydibenzoyl methane (Neo Heliopan®357)
3-(4'-sulfo)benzylidene bornan-2-one and salts
2-ethylhexyl-2-cyano-3,3-diphenyl acrylate (Neo Heliopan®303)
N-[(2 and 4)-[2-(oxoborn-3-ylidene) methyl]benzyl]acrylamide polymer
p-methoxycinnamic acid-2-ethylhexyl ester (Neo Heliopan®AV)
p-aminobenzoic acid ethyl ester (25 mol) ethoxylated
p-methoxycinnamic acid isoamyl ester (Neo Heliopan®E1000)
2,4,6-trianilino-(p-carbo-2'-ethylhexyl-1'-oxy)-1,3,5-triazine (Uvinul®T150)
2-(2H-benzotriazol-2-yl)-4-methyl-6-(2-methyl-3(1,3,3,3-tetramethyl-1-(trimethylsilyl)oxy)disiloxyanyl)propyl) phenol (Mexoryl®XL)
4,4'-[(6-[4-(1,1-dimethyl)aminocarbonyl)phenylamino]-1-1,3,5-triazine-2,4-diyl)diimino]-bis-(benzoic acid-2-ethylhexyl ester) (Uvasorb®HEB)
3-(4'-methyl benzylidene)-d,l-camphor (Neo Heliopan®MBC)
3-benzylidene camphor
salicylic acid-2-ethylhexyl ester (Neo Heliopan®OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl)phenol) (Tinosorb®M)
phenylene bis-benzimidazyl tetrasulfonic acid disodium salt (Neo Heliopan®AP)
2,4-bis-[{(4-(2-ethylhexyloxy)-2-hydroxy}phenyl]-6-(4-methoxyphenyl)-1,3,5-triazine, (Tinosorb®S)
benzylidene malonate polysiloxane (Parsol SLX)
menthyl anthranilate (Neo Heliopan®MA)
2-(4-diethylamino-2-hydroxybenzoyl)benzoic acid hexyl ester (Uvinul® A Plus)
indanylidene compounds according to DE 100 55 940 (WO 02/38537)

Formulations or products according to the present invention in the form of sunscreen formulations (as described above) preferably have a SPF (sun protection factor) of equal or greater than 15, preferably of equal or greater than 20, more preferably of equal or greater than 30.

Preferred formulations or products of the present invention in the form of sunscreen formulations comprise 4-(1,1-dimethylethyl)-4'-methoxydibenzoylmethane (4-t-butyl-4'-methoxydibenzoyl methane; avobenzone), preferably in an amount in the range of from 0.2 to 10 wt.-%, more preferred in the range of from 0.5 to 5 wt.-%, based on the total weight of the sunscreen formulation.

In particularly preferred sunscreen formulations the pH-value is in the range of from pH 4 to pH 8, preferably from pH 4 to 6.5.

Formulations and (cosmetic or pharmaceutical) products according to the invention preferably further comprise
one or more antioxidants and/or
one or more cooling agents and/or
one or more antimicrobials and/or
one or more hair growth inhibitors.

Particularly preferred are antioxidants which are suitable for cosmetic and/or pharmaceutical/dermatological applications. As reactive oxygen species play an important role in inflammation, further benefits can be achieved in this way.

Principally, any antioxidants which are suitable or usual for cosmetic and/or pharmaceutical/dermatological uses may be used. The antioxidants are preferably selected from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. alpha-carotene, beta-carotene, lycopene) and derivatives thereof, chlorogenic acid and derivatives thereof, liponic acid and derivatives thereof (e.g. dihydroliponic acid), aurothioglucose, propylthiouracil and other thiols (e.g. thioredoxin, glutathione, cysteine, cystine, cystamine and glycosyl, N-acetyl, methyl, ethyl, propyl, amyl, butyl and lauryl, palmitoyl, oleyl, gamma-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), (metal) chelators, e.g. alpha-hydroxy-fatty acids, palmitic acid, phytic acid, lactoferrin, alpha-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. gamma-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate, ascorbyl glycosides, such as e.g. 6-O-acyl-2-O-alpha-D-glucopyranosyl-L-ascorbic acid, 6-O-acyl-2-O-beta-D-glucopyranosyl-L-ascorbic acid, 2-O-alpha-D-glucopyranosyl-L-ascorbic acid or 2-O-beta-D-glucopyranosyl-L-ascorbic acid), tocopherols and derivatives thereof (e.g. vitamin E acetate), vitamin A and derivatives thereof (vitamin A palmitate) as well as coniferylbenzoate of benzoin resin, rutic acid and derivatives thereof, alpha-glucosylrutin, quercetin and derivatives thereof, rosemary acid, carnosol, carnosol acid, resveratrol, caffeic acid and derivatives thereof, sinapic acid and derivatives thereof, ferulic acid and derivatives thereof, furfurylideneglucitol, curcuminoids, butylhydroxytoluene, butylhydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$), selenium and derivatives thereof (e.g. selenium methionine), stilbenes and derivatives thereof (e.g. stilbene oxide, trans-stilbene oxide) and derivatives (salts, esters, ethers, sugars, nucleotides, nucleosides, peptides and lipids) of these active compounds mentioned or antioxidatively active extracts or fractions from plants, such as e.g. green tea, rooibos, honeybush, grape, rosemary, sage, Melissa, thyme, lavender, olive, oats, cocoa, ginkgo, ginseng, liquorice, honeysuckle, Sophora, Pueraria, Pinus, Citrus, Phyllanthus emblica or St. John's wort.

The total amount of antioxidants in a formulation or product according to the invention is preferably in the range of from 0.01 to 20 wt. %, preferably from 0.05 to 10 wt. %, in particular from 0.2 to 5 wt. %, based on the total weight of the formulation or product.

Also preferred are formulations and products according to the present invention comprising one or more cooling agents (as described above) wherein the cooling agent(s) is/are selected from the group consisting of: menthol, preferably l-menthol, menthone glycerin acetal (trade name: FrescolaC-MGA), menthyl lactate (preferably l-menthyl lactate, in particular l-menthyl-l-lactate, trade name: Frescolat®ML), substituted menthyl-3-carboxylic acid amide (e.g. menthyl-3-carboxylic acid-N-ethylamide), 2-isopropyl-N-2,3-trimethylbutanamide, substituted cyclohexane carboxylic acid amide, 3-menthoxypropane-1,2-diol, 2-hydroxyethyl-menthylcarbonate, 2-hydroxypropylmenthylcarbonate, N-acetyl glycine menthyl ester, Isopulegol, menthyl hydroxycarboxylic acid ester (e.g. menthyl-3-hydroxybutyrate), monomenthylsuccinate, 2-mercaptocyclodecanone, menthyl-2-pyrrolidin-5-one carboxylate, 2,3-dihydroxy-p-menthane, 3,3,5-trimethyl cyclohexanone glycerine ketal, 3-menthyl-3,6-di- and -trioxa Ikanoate, 3-menthylmethoxy acetate, N-(4-cyanomethylphenyl)-p-menthanecarboxamide, N-(4-cyanophenyl)-p-menthanecarboxamide and Icilin.

Particularly preferred cooling agents are l-menthol, menthone glycerine acetal (trade name: Frescolat®MGA), menthyl lactate (preferably l-menthyl lactate, in particular l-menthyl-l-lactate, trade name: Frescolat®ML), 3-menthoxy propane-1,2-diol, 2-hydroxyethyl menthyl carbonate, 2-hydroxypropyl menthyl carbonate. Most preferred is l-menthyl-l-lactate.

For certain applications formulations or products according to the present invention are preferred which further comprise one, two or more compounds of the group consisting of: glycerol, 1,2-propanediol, 1,3-propanediol, 1,2-butanediol, 1,3-butanediol, 1,4-butanediol, 2,3-butanediol, 1,2-pentanediol, 1,5-pentanediol, 1,2-hexanediol, 1,6-hexanediol, 1,2-octanediol, 1,8-octanediol, 2-methylpentane-2,4-diol, 2,5-hexanediol, 3,6-octanediol, 2-ethyl-1,3-hexanediol, 1,3-octanediol, 1,2-decanediol, 1,3-decanediol, 1,2-dodecandiol, 1,2-tetradecandiol.

Formulations and products of the present invention may additionally comprise one or more antimicrobials (as described above), such as chitosan, totarol, farnesol, glycerol monolaurate, arylalkyl alcohols, such as e.g. 4-methyl-4-phenyl-2-pentanol and its derivatives (DE 101 43 434, in particular 4-methyl-4-phenyl-2-pentanol), muguet alcohol (2,2-dimethyl-3-phenylpropanol), other arylalkyl alcohols (e.g. as disclosed in DE 44 47 361, DE 103 30 697, U.S. Pat. No. 4,110,430 or EP 1 157 687), 2-butyloctanoic acid, 2-hexyldecanoic acid, p-anisic acid, essential oils with antimicrobial properties and isolates from essential oils with antimicrobial properties like e.g. thymol or eugenol, perfume oils or single aroma chemicals with antimicrobial activity, polyglycerol esters, such as e.g. polyglyceryl 3-caprylates, or combinations of the substances mentioned, which are generally employed, inter alia, against underarm odor, foot odor, acne or dandruff formation.

In some cases a formulation or product of the present may also comprise one or more (metal) chelators. (Metal) chelators which are preferably to be employed are, inter alia, alpha-hydroxy fatty acids, phytic acid, lactoferrin, alpha-hydroxy acids, such as, inter alia, citric acid, lactic acid and malic acid, and humic acids, bile acids, bile extracts, bilirubin, biliverdin, trisodium methylglycinediacetic acid, tetrasodium glutamate diacetate or EDTA, EGTA and derivatives thereof.

Formulations and products according to the present invention may also comprise one or more anti-cellulite and/or lipolytic agents as well as agents enhancing or boosting the activity of anti-cellulite agents.

Anti-cellulite agents and lipolytic agents are preferably selected from the group consisting of those described in WO 2007/077541, and beta-adrenergic receptor agonists such as synephrine and its derivatives.

Agents enhancing or boosting the activity of anti-cellulite agents, in particular agents which stimulate and/or depolarise C nerve fibres, are preferably selected from the group consisting of capsaicin and derivatives thereof, vanillyl-nonylamid and derivatives thereof, L-carnitine, coenzym A, isoflavonoides, soy extracts, ananas extract and conjugated linoleic acid.

Formulations and products according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, plants and plant parts of for example the genera dandelion (Leontodon or Taraxacum), Orthosiphon, Vitex, Coffea, Paullinia, Theobroma, Asiasarum, Cucurbita or Styphnolobium, Serenoa repens (saw palmetto), Sophora flavescens, Pygeum africanum, Panicum miliaceum, Cimicifuga racemosa, Glycine max, Eugenia caryophyllata, Cotinus coggygria, Hibiscus rosa-sinensis, Camellia sinensis, Ilex paraguariensis, licorice, grape, apple, barley or hops or/and hydrolysates from rice or wheat.

Alternatively, formulations and products according to the present invention may comprise one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera Chondrus, Gloiopeltis, Ceramium, Durvillea, Glycine max, Sanguisorba officinalis, Calendula officinalis, Hamamelis virginiana, Arnica montana, Salix alba, Hypericum perforatum or Gymnema sylvestre.

Formulations and products according to the present invention may also comprise one or more compatible solutes. Preferred compatible solutes are such as described in WO 01/76572, particularly dimyo-inositol phospate (DIP), diglycerin phospate (DGP), di-myo-inositol phosphate (DIP), cyclic 2,3 diphosphoglycerate (cDPG), 1,1-di-glycerol phosphate (DG P), beta-mannosyl glycerate (firoin), beta-mannosyl glyceramide (firoin-A) and di-mannosyl-di-inositol phosphate (DMIP) and ectoine and ectoine-derivatives, as described in EP 0 553 884, EP 0 671 161 and WO 94/15923, in particular ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid).

Preferably, the total amount of compatible solutes is in the range of from 0.05 to 10 wt.-%, preferably from 0.1 to 5 wt.-%, based on the total weight of the formulation or product.

Dental care compositions (as a preferred example of an oral care product according to the invention (as described above)) in general comprise an abrasive system (abrasive or polishing agent), such as e.g. silicas, calcium carbonates, calcium phosphates, aluminium oxides and/or hydroxyapatites, surface-active substances, such as e.g. sodium lauryl sulfate, sodium lauryl sarcosinate and/or cocamidopropyl betaine, moisture-retaining agents, such as e.g. glycerol and/or sorbitol, thickening agents, such as e.g. carboxymethylcellulose, polyethylene glycols, carrageenan and/or Laponite®, sweeteners, such as e.g. saccharin, flavour correctants for unpleasant taste impressions, flavour correctants for further, as a rule not unpleasant taste impressions, flavour-modulating substances (e.g. inositol phosphate, nucleotides, such as guanosine monophosphate, adenosine monophosphate or other substances, such as sodium glutamate or 2-phenoxypropionic acid), cooling active compounds, such as e.g. menthol derivatives (e.g. L-menthyl lactate, L-menthyl alkyl carbonates, menthone ketals, menthanecarboxylic acid amides), 2,2,2-trialkylacetic acid amides (e.g. 2,2-diisopropylpropionic acid methylamide), icilin and icilin derivatives, stabilizers and active compounds, such as e.g. sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, chlorhexidine, cetylpyridinium chloride, aluminium lactate, potassium citrate, potassium nitrate, potassium chloride, strontium chloride, hydrogen peroxide, aromas, sodium bicarbonate and/or odour to correctants.

Formulations or products according to the invention in the form of chewing gums or, in particular, dental care chewing gums comprise chewing gum bases which comprise elastomers, such as, for example, polyvinyl acetates (PVA), polyethylenes, (low or medium molecular weight) polyisobutenes (FIB), polybutadienes, isobutene-isoprene copolymers (butyl rubber), polyvinyl ethyl ethers (PVE), polyvinyl butyl ethers, copolymers of vinyl esters and vinyl ethers, styrene/butadiene copolymers (styrene/butadiene rubber, SBR) or vinyl elastomers, e.g. based on vinyl acetate/vinyl laurate, vinyl acetate/vinyl stearate or ethylene/vinyl acetate, and mixtures of the elastomers mentioned, as described, for example, in EP 0 242 325, U.S. Pat. Nos. 4,518,615, 5,093,136, 5,266,336 5,601,858 or U.S. Pat. No. 6,986,709. In addition, chewing gum bases comprise further constituents, such as, for example, sugars, sugar substitutes or sweet-tasing substances in particular those described in WO 2009/21558, (mineral) fillers, plasticizers, emulsifiers, antioxidants, waxes, fats or fatty oils, such as, for example, hardened (hydrogenated) plant or animal fats, and mono-, di- or triglycerides. Suitable (mineral) fillers are, for example, calcium carbonate, titanium dioxide, silicon dioxide, talc, aluminium oxide, dicalcium phosphate, tricalcium phosphate, magnesium hydroxide and mixtures thereof. Suitable plasticizers or agents for preventing sticking (detackifiers) are, for example, lanolin, stearic acid, sodium stearate, ethyl acetate, diacetin (glycerol diacetate), triacetin (glycerol triacetate) and triethyl citrate. Suitable waxes are, for example, paraffin waxes, candelilla wax, carnauba wax, microcrystalline waxes and polyethylene waxes. Suitable emulsifiers are, for example, phosphatides, such as lecithin, and mono- and diglycerides of fatty acids, e.g. glycerol monostearate.

Formulations or products according to the invention (in particular those which are in the form of an oral care product or a product with irritation-reducing action on the respiratory tract) preferably additionally comprise one or more aroma and/or flavouring substances, such as essential oils and extracts, tinctures and balsams, such as, for example, anisole, basil oil, bergamot oil, bitter almond oil, camphor oil, citronella oil, lemon oil; Eucalyptus citriodora oil, eucalyptus oil, fennel oil, grapefruit oil, camomile oil, spearmint oil, caraway oil, lime oil, mandarin oil, nutmeg oil (in particular nutmeg blossom oil=maces oil, mace oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

It is of particular advantage if said formulations or products comprise at least one aroma substance, preferably 2, 3, 4, 5, 6, 7, 8, 9, 10 or more aroma substances, chosen from the following group: menthol (preferably l-menthol and/or racemic menthol), anethole, anisole, anisaldehyde, anisyl alcohol, (racemic) neomenthol, eucalyptol (1,8-cineol), menthone (preferably L-menthone), isomenthone (preferably D-isomenthone), isopulegol, menthyl acetate (preferably L-menthyl acetate), menthyl propionate, carvone (preferably (−)-carvone, optionally as a constituent of a spearmint oil), methyl salicylate (optionally as a constituent of a wintergreen oil), eugenol acetate, isoeugenol methyl ether, beta-homocyclocitral, eugenol, isobutyraldehyde, 3-octanol, dimethyl sulfide, hexanol, hexanal, trans-2-hexenal, cis-3-hexenol, 4-terpineol, piperitone, linalool, 8-ocimenyl acetate, isoamyl alcohol, isovaleraldehyde, alpha-pinene, beta-pinene, limonene (preferably D-limonene, optionally as a constituent of an essential oil), piperitone, trans-sabinene hydrate, menthofuran, caryophyllene, germacrene D, cinnamaldehyde, mint lactone, thymol, gamma-octalactone, gamma-nonalactone, gamma-decalactone, (1,3E,5Z)-undecatriene, 2-butanone, ethyl formate, 3-octyl acetate, isoamyl isovalerate, cis- and trans-carvyl acetate, p-cymol, damascenone, damascone, cis-rose oxide, trans-rose oxide, fenchol, acetaldehyde diethyl acetal, 1-ethoxyethyl acetate, cis-4-heptenal, cis-jasmone, methyl dihydrojasmonate, 2'-hydroxypropiophenone, menthyl methyl ether, myrtenyl acetate, 2-phenylethyl alcohol, 2-phenylethyl isobutyrate, 2-phenylethyl isovalerate, geraniol, nerol and viridiflorol.

Preferably, a formulation or product according to the invention comprises a mixture of flavouring and/or aroma substances which imparts to said formulation or product an overall herbal (herb-like), minty, cinnamon-like, clove-like, wintergreen and/or fruity character.

A further formulation, cosmetic product or pharmaceutical product according to the invention preferably comprises a substance or substance mixture having an irritating, preferably a skin-irritating, action, wherein the total amount of bisabolol and [6]-paradol in the formulation, cosmetic product or pharmaceutical product is sufficient to reduce, eliminate or suppress the irritating action of the substance or substance mixture.

The present invention also provides the use of a formulation, a cosmetic product or a pharmaceutical product as described above, for prophylaxis and/or treatment of irritation, preferably of skin irritation. Preferably, said use is a non-therapeutic use.

The invention likewise provides the use of a formulation as described above for the to preparation of a pharmaceutical product for prophylaxis and/or treatment of irritation, preferably of skin irritation.

In addition, the present invention also relates to the use of a formulation as described above for the preparation of a cosmetic product.

The invention also provides the use, preferably the non-therapeutic use, of a formulation, a cosmetic product or a pharmaceutical product according to the invention (as described above), for reducing, eliminating or suppressing the irritating action, preferably the skin-irritating action, of a substance or substance mixture.

The advantage of the uses according to the invention (as described above) is that due to the synergistic effect of [6]-paradol and bisabolol contained in the formulation or the product according to the invention, relatively low total amounts of irritating agents are sufficient in order to provide a skin irritation-reducing action. This reduces the probability of a renewed allergic reaction and can include cost advantages and contribute towards protecting the environment.

The present invention also provides a process for the preparation of a formulation, a cosmetic product or a pharmaceutical product according to the invention (as described above), with the following steps:
provision of [6]-paradol,
provision of bisabolol, and
mixing of provided [6]-paradol and bisabolol, so that the amounts of [6]-paradol and bisabolol in the mixture are adjusted such that the irritation-reducing action, preferably the skin irritation-reducing action, of these contents is increased synergistically.

The present invention likewise provides a (cosmetic or therapeutic) method, preferably a cosmetic method, for prophylaxis of skin irritation, with the following steps:
provision of a formulation, a cosmetic product or a pharmaceutical product according to the invention (as described above) and
application of the provided formulation, cosmetic product or pharmaceutical product to non-irritated skin in an active amount.

The invention furthermore provides a cosmetic or therapeutic method, preferably a cosmetic method, for treatment of skin irritation, with the following steps:
provision of a formulation, a cosmetic product or a pharmaceutical product according to the invention (as described above) and
application of the provided formulation, cosmetic product or pharmaceutical product to irritated skin in an active amount.

A further aspect of the present invention relates to a method for reducing, eliminating or suppressing the irritating, preferably the skin-irritating, action of a substance or substance mixture,
with the following steps:
(I) provision of a substance or substance mixture having an irritating, preferably a skin-irritating, action,
(II) provision of [6]-paradol,
(III) provision of bisabolol, and
(IV) mixing provided [6]-paradol and bisabolol with the substance or substance mixture having an irritating, preferably a skin-irritating, action, so that the irritating action is reduced, eliminated or suppressed.

One advantage of the method mentioned last is that the skin-irritating action of substances or substance mixtures can be moderated in a way that the substances or substance mixtures are accessible for uses they were hitherto not available. On the basis of this method, if applicable, higher concentrations of a skin-irritating substance or substance mixture can be employed in uses wherein the skin may be contacted with the to skin-irritating substance or substance mixture. In this context, it is particularly preferable, if, on the basis of this method, the skin-irritating action of the skin-irritating substance(s) is eliminated completely (i.e. if it no longer exists) or is suppressed completely (i.e. if it no longer has an effect). The method according to the invention mentioned last can be employed, for example, against the skin-irritating action of detergents and allergy-inducing substances.

For aforementioned methods and uses according to the invention, the weight ratios of [6]-paradol and bisabolol and the total amounts thereof as described above likewise apply.

The present invention also provides a kit comprising (i) a formulation, cosmetic product or pharmaceutical product according to the invention (as described above) and, spatially separated, (ii) one or more substances or substance mixtures having an irritating, preferably a skin-irritating, action.

Using such a kit, after a series of tests of several (skin-irritating) substances on a particular area of skin, said area of skin can be treated for regeneration with (i) the formulations, the cosmetic or the pharmaceutical product, if necessary.

Preferred embodiments and further aspects of the present invention emerge from the attached patent claims and the following examples, the examples not being intended to limit the scope of the present invention.

Unless indicated otherwise, all data, in particular ratios and percentages, refer to the weight.

EXAMPLE 1

Synthesis of [6]-paradol

EXAMPLE 1.1

Synthesis of 1-(4-Hydroxy-3-methoxy-phenyl)-dec-1-en-3-one 100 g potassium hydroxide were dissolved in 500 g of methanol and heated up to reflux under stirring. A solution of 142 g of nonanone and 152 g of vanillin in 120 g of methanol were subsequently added continuously over a period of 1 hour. After that, the mixture was stirred for further 24 hours at the same temperature. After distilling 400 g of methanol from the mixture in vacuo, 400 g of toluene were added to the remaining residue, and after cooling to approximately 30-40° C. additionally 800 g of water were added. The mixture was then acidified with approximately 380 g of diluted sulphuric acid (20% in water) to a pH value of 4-5. After phase separation, the organic phase was washed with 200 g of water. After distillation, 120 g of the intermediate product 1-(4-hydroxy-3-methoxy-phenyl)-dec-1-en-3-one were obtained. Melting point: 45° C., yield: 42% of theory.

EXAMPLE 1.2

Synthesis of [6]-Paradol (1-(4-hydroxy-3-methoxy-phenyl)-decan-3-one)

120 g of 1-(4-hydroxy-3-methoxy-phenyl)-dec-1-en-3-one as obtained in Example 1.1 were dissolved in 240 g of ethanol, 1 g of Raney-Nickel was added and hydrogenated at 20 bar and 70° C. over a period of 4 hours. The catalyst was filtered off and the remaining filtrate was distilled giving 110 g product. For elimination of the remaining approximately 3% by-products, said by-products essentially consisting of the corresponding alcohol 1-(4-hydroxy-3-methoxy-phenyl)-decan-3-ol obtained by overhydrogenation, the product was distilled over 1 g boric acid. Thus, 100 g [6]-paradol with a purity of >99% were obtained. Melting point: 29° C., yield: 77% of theory.

EXAMPLE 2

Anti-Prostaglandin $E_2$ ($PGE_2$) Assay $PGE_2$ is an important inflammatory mediator in the skin. Thus, the inhibiting effect of [6]-paradol and related compounds on (A23187-induced) $PGE_2$ release of human skin cells (keratinocytes) is investigated.

Primary human epidermal keratinocytes are seeded into a 96 well microplate and are cultured in KGM medium to 60-80% confluency. Afterwards, the KGM medium is substituted by KGM medium depleted of hydrocortisone but containing the test compounds (test compound solutions are applied in medium in three different concentrations, each as a triple determination in three different wells, e.g. for [6]-paradol: in experiment 1 the following concentrations were used: 20 µM, 2 µM and 0.2 µM, in experiment 2 the following concentrations were used: 10 µM, 1 µM and 0.1 µM and in experiment 3 the following concentrations were used: 2.5 µM, 0.25 µM and 0.025 µM.

The cells are incubated for 30 minutes. Then, $PGE_2$ release is stimulated by addition of 2 µM A23187 calcium ionophore. After further 30 min incubation, the $PGE_2$ content of the supernatant is quantified in an ELISA ($PGE_2$ Enzyme Immunoassay System from GE Healthcare).

Results:

TABLE 1

PGE$_2$ inhibitory activity of different test compounds

| Test compound | Test concentration [µM] | IC50 [µM] | Optimum [µM] | Maximum PGE$_2$ inhibition [%] |
|---|---|---|---|---|
| [6]-Paradol | 0.025-20 | 0.13 ± 0.11 | 5 | 90-100 |
| [6]-Gingerol | 0.05-10 | 3.47 ± 4.08 | 5 | ~30 |
| [8]-Gingerol | 0.02-20 | 1.42 ± 0.67 | 20 | ~70 |
| [8]-Paradol | 0.1-20 | 1.48 ± 1.21 | 10 | 80-100 |

The results set out above were obtained from at least two independent experiments. $PGE_2$ inhibition was calculated in comparison to the calcium ionophore A23187-induced stimulated control (without addition of test compounds).

Unexpectedly, [6]-paradol is the most active of the tested compounds. It exhibits the lowest 1050 (50% of $PGE_2$ release is inhibited) with 0.13 µM and gives (at 5 µM) a maximum $PGE_2$ inhibition of 90-100%.

EXAMPLE 3

Comparison of Redness Reduction

The redness reducing activity of [6]-paradol per se (active compound A), bisabolol per se (active compound B) and two mixtures of bisabolol and [6]-paradol (active compound combinations C and D) has been determined in a sodium dodecyl sulphate (SDS) irritation study. The formulations with active compound combinations C and D (see table 2 below) are preferred formulations according to the present invention as described above.

Procedure:

The SDS inflammation test was used as test model. The study was conducted on the inside under-arm of 10 caucasian subjects (age: between 18 and 60 years, test area per test formulation: 3×3 cm). The reddening of the skin was recorded with a Minolta-Chromameter CR 300 via the a* value of the La'b' colour system, which describes the position on the red-green axis.

Baseline measurements were taken and the erythema was induced by a 24-hour occlusive treatment with 2% SDS. Redness was measured directly after the removal of the occlusive patches (day 0, after SDS).

Then, the skin was treated with 0.05 ml of the test formulation in question (see below) two times daily (morning and evening with 8 hours in-between) for 3 days. 3 h after the last application on day 1 and 3, the reddening of the skin was determined and the erythema (redness) percentage was calculated.

Formulations:

For the study, a defined amount of active compound combinations C and D were incorporated into hydrodispersion gels. The active compounds A and B were, for comparison purposes, incorporated into separate hydrodispersion gels.

TABLE 2

Composition of the formulations (data in %):

| Raw material name (Manufacturer) | INCI | Placebo | with [6]-Paradol (active compound A) | with Bisabolol (active compound B) | with active compound combination C | with active compound combination D |
|---|---|---|---|---|---|---|
| Dragosantol 100 (Symrise) | Bisabolol | \ | \ | 0.1 | 0.065 | 0.039 |
| [6]-Paradol as 0.2% solution in PCL Liquid 100 | | \ | 1.0* | \ | 0.35** | 0.61*** |
| Abil 350 (Evonik Degussa) | Dimethicone | 0.5 | 0.5 | 0.5 | 0.5 | 0.5 |
| Eutanol G (Cognis) | Octyldecanol | 3.5 | 3.5 | 3.5 | 3.5 | 3.5 |

TABLE 2-continued

Composition of the formulations (data in %):

| Raw material name (Manufacturer) | INCI | Placebo | formulation with [6]-Paradol (active compound A) | with Bisabolol (active compound B) | with active compound combination C | with active compound combination D |
|---|---|---|---|---|---|---|
| Glycerin, 85% (Symrise) | Glycerin | 1.0 | 1.0 | 1.0 | 1.0 | 1.0 |
| Glycacil 2000 (6% IPBC) (Lonza) | Iodopropynyl Butylcarbamate | 0.3 | 0.3 | 0.3 | 0.3 | 0.3 |
| Hydrolite-5 (Symrise) | 1,2-Pentylene Glycol | 1.0 | 1.0 | 1.0 | 1.0 | 1.0 |
| Lanette O (Cognis) | Cetearyl Alcohol | 2.0 | 2.0 | 2.0 | 2.0 | 2.0 |
| NaOH solution, 10% | Sodium Hydroxide | 0.5 | 0.5 | 0.5 | 0.5 | 0.5 |
| Paraffin oil 5° E | Mineral oil | 3.0 | 3.0 | 3.0 | 3.0 | 3.0 |
| PCL Liquid 100 (Symrise) | Cetearyl Octanoate | 3.00 | 2.00 | 3.00 | 2.65 | 2.40 |
| Pemulen TR1 (Noveon) | Acrylates/C10-30 Alkyl Acrylate Crosspolymer | 0.2 | 0.2 | 0.2 | 0.2 | 0.2 |
| SymDiol 68 (Symrise) | 1,2-Heaxanediol, Caprylyl Glycol | 0.6 | 0.6 | 0.6 | 0.6 | 0.6 |
| SymMollient W/S (Symrise) | Trideceth-9, PEG-5 Isononanoate, Water (Aqua) | 0.5 | 0.5 | 0.5 | 0.5 | 0.5 |
| Ultrez-21 (Noveon) | Acrylates/C10-30 Alkyl Acrylate Crosspolymer | 0.05 | 0.05 | 0.05 | 0.05 | 0.05 |
| Water | Water | ad 100 | ad 100 | ad 100 | ad 100 | ad 100 | pH: 6.1-6.2
*the formulation comprises 0.0020% of [6]-paradol
**the formulation comprises 0.0007% of [6]-paradol
***the formulation comprises 0.0012% of [6]-paradol Results:

The results of the measurement of redness (a* value) in the SDS irritation study on the formulations with active compound combinations C and D and active compounds A and B per se, clearly show synergistic effects of the formulations with C and D (see table 3 below). This test series thus shows by way of example that the active compound mixtures, i.e. formulations according to the invention, have a (significantly) synergistically to improved redness reducing action compared with the formulations with active compounds A ([6]-paradol) and B (bisabolol) per se.

TABLE 3

Mean erythema (redness, a* value) in %

| Test sample | Before SDS ^ | After SDS (day 0) ^^ | Day 1 ^^^ | Day 3 |
|---|---|---|---|---|
| Formulation with active compound A (see table 2) | 0 | 100 | 137.3 | 71.8 |
| Formulation with active compound B (see table 2) | 0 | 100 | 128.6 | 76.6 |
| Formulation with active compound combination C (see table 2) | 0 | 100 | 96.0 | 58.8 |
| Formulation with active compound combination D (see table 2) | 0 | 100 | 108.8 | 58.4 |
| Placebo | 0 | 100 | 134.8 | 82.3 |

^ a* value baseline (before SDS) = 0% erythma
^^ after SDS (day 0) = a* value after SDS − a* value baseline = 100% erythma
^^^ day X = (a* value day X − a* value baseline)/(a* value after SDS − a* value baseline) × 100

In contrast to placebo, to the formulation with active compound A ([6]-paradol), the formulation with active compound B (bisabolol) and the formulation with active compound combination D, the formulation with active compound combination C already exhibits redness reduction on day 1 while the others show increasing redness with this test design. The formulation with compound combination C is thus a particularly preferred formulation according to the present invention.

The synergy index (SI) values according to Kull for the redness reduction in the SDS inflammation test for compound combinations C and D after a treatment time of 1 and 3 days are calculated as follows:

TABLE 4

|  | Formulation with active compound A 0.002% [6]-Paradol* | Formulation with active compound B 0.1% Bisabolol | Formulation with active compound combination C 0.0007% [6]-Paradol** and 0.065% Bisabolol | Formulation with active compound combination D 0.0012% [6]-Paradol*** and 0.039% Bisabolol |
|---|---|---|---|---|
| Mean erythema in % (day 1) | 137.3 | 128.6 | 96.0 | 108.8 |
| Mean erythema in % (day 3) | 71.8 | 76.6 | 58.8 | 58.4 |

Kull's equation: $SI = C \times D/A + C \times E/B$

|  | Formulation with active compound combination C | | Formulation with active compound combination D | |
|---|---|---|---|---|
|  | Day 1 | Day 3 | Day 1 | Day 3 |
| A: Mean erythema in % for the formulation with active compound A | 137.3 | 71.8 | 137.3 | 71.8 |
| B: Mean erythema in % for the formulation with active compound B | 128.6 | 76.6 | 128.6 | 76.6 |
| C: Mean erythema in % for the formulation with compound composition C/D | 96.0 | 58.8 | 108.8 | 58.4 |
| D: Factor = content of [6]-paradol in the formulation with compound composition C/ content of [6]-paradol in the formulation with active compound A | 0.35 | 0.35 | 0.61 | 0.61 |
| E: Factor = content of bisabolol in the formulation with compound composition D/ content of bisabolol in the formulation with active compound B | 0.65 | 0.65 | 0.39 | 0.39 |
| SI: Synergy index | 0.730 | 0.786 | 0.813 | 0.793 |

*corresponding to a dosage of 1.0% of a 2% solution of [6]-paradol in PCL Liquid 100
**corresponding to a dosage of 0.35% of a 2% solution of [6]-paradol in PCL Liquid 100
***corresponding to a dosage of 0.61% of a 2% solution of [6]-paradol in PCL Liquid 100

The calculation was performed with the aid of known literature (D. C. Steinberg, Cosmetics & Toiletries 2000, 115 (11), 59-62 and F. C. Kull et al., Applied Microbiology 1961, 9, 538-541). According to Kull's equation, evidence of a synergy effect results from SI values of <1.

The calculated SI values of 0.730 and 0.786 for the formulation with compound combination C and of 0.813 and 0.793 for the formulation with compound combination D clearly show that the mixtures are highly synergistic combinations of [6]-paradol and bisabolol.

EXAMPLES 4-14

Skin and Hair Care Products

In table 5 below
4=Skin-lightening day care fluid O/W
5=Shaving Cream O/W
6=After shave hydro gel
7=After-Sun spray O/W
8=Sunscreen lotion (O/W), broad-band protection
9=W/O night cream
10=Anti-dandruff shampoo
11=Calming hair conditioner
12=Barrier repair cream O/W
13=Calming Balm
14=Antiperspirant pump spray

TABLE 5

| Raw Material Name (Manufacturer) | INCI | % | | | | | | | | | | |
|---|---|---|---|---|---|---|---|---|---|---|---|---|
| | | 4 | 5 | 6 | 7 | 8 | 9 | 10 | 11 | 12 | 13 | 14 |
| -(-Alpha-)-Bisabolol, natural (Symrise) | Bisabolol | | 0.396 | | | | 0.198 | 0.495 | | 0.049 | 0.199 | 0.099 |
| Dragosantol 100 (Symrise) | Bisabolol | 0.199 | | 0.0995 | 0.098 | 0.0495 | | | 0.297 | | | |
| [6]-Paradol | | 0.001 | 0.004 | 0.0005 | 0.002 | 0.0005 | 0.002 | 0.005 | 0.003 | 0.001 | 0.001 | 0.001 |
| Abil 350 (Degussa-Goldschmidt) | Dimethicone | 0.5 | | | | | | | | 0.5 | 2.0 | |
| Allantoin (Merck) | Allantoin | | | 0.1 | | | | | | | 0.1 | |
| Aloe Vera Gel Concentrate 10/1 (Symrise) | Water (Aqua), Aloe Barbadensis Leaf Juice | | | 1.0 | | | 3.0 | | 0.5 | | | |
| Alugel 34 TH (Baerlocher) | Aluminium Stearate | | | | | | | 1.0 | | | | |
| Arbutin (Sabinsa) | beta-Arbutin | 1.0 | | | | | | | | | | |
| Arylpon F (Cognis) | Laureth-2 | | | | | | | | 2.0 | | | |
| Avocado Oil (Symrise) | Persea Gratissima (Avocado) Oil | | | | | 3.0 | | | | | | |
| Carbopol ETD 2050 (Noveon) | Carbomer | 0.2 | | | | 0.2 | | | | | | |
| Carbopol Ultrez 21 (Noveon) | Acrylates/C10-30 Alkyl Acrylate Crosspolymer | | | 0.4 | | | | | | | 0.6 | |
| CeramideBio (Symrise) | Cetylhydroxy proline Palmitamide | | | | | | | | | 0.5 | | |
| Ceramide SL (Sino Lion) | Hydroxyethyl Palmityl Oxyhydroxypropyl Palmitamide | | | | | | 0.1 | | | | | |
| Citric Acid 10% sol. | Citric Acid | | | | | | | | | 0.5 | | |
| Covi-Ox T-70 (Cognis) | Tocopherol | | | | | 0.1 | | | | | | |
| Crinipan AD (Symrise) | Climbazole | | | | | | | | 0.3 | | | |
| Dehyquart A CA (Cognis) | Cetrimonium Chloride | | | | | | | | 4.0 | | | |
| Dow Corning 246 Fluid (Dow Corning) | Cyclohexasiloxane, Cyclopentasiloxane | | | | 2.0 | 2.0 | | | | | | |
| D-Panthenol (BASF) | Panthenol | | | 0.5 | 1.0 | | 0.5 | | 1.0 | | | 1.0 |

TABLE 5-continued

| Raw Material Name (Manufacturer) | INCI | 4 | 5 | 6 | 7 | 8 | 9 | 10 | 11 | 12 | 13 | 14 |
|---|---|---|---|---|---|---|---|---|---|---|---|---|
| Dracorin CE (Symrise) | Glyceryl Stearate Citrate | | | | | | | | | 1.5 | | |
| Dracorin GMS (Symrise) | Glyceryl Stearate | | | | | | | | | 2.0 | | |
| Dracorin GOC (Symrise) | Glyceryl Oleate Citrate, Caprylic/Capric Triglyceride | | | | 2.0 | | | | | | | |
| Dragocid Liquid (Symrise) | Phenoxyethanol, Methylparaben, Ethylparaben, Butylparaben, Propylparaben, Isobutylparaben | 0.8 | | | | 0.7 | 0.8 | 0.7 | 0.8 | 0.8 | | |
| Dragoderm (Symrise) | Glycerin, *Triticum Vulgare* (Wheat) Gluten, Water (Aqua) | | | | | | | | 2.0 | | | |
| Dragosan W/O Liquid (Symrise) | Polyglyceryl-3-Polyricinoleate, Sorbitan Isostearate | | | | | | 1.0 | | | | | |
| Dragosan W/O P (Symrise) | Sorbitan Isostearate, Hydrogenated Castor Oil, Ceresin, Beeswax (Cera Alba) | | | | | | 6.0 | | | | | |
| Dragoxat 89 (Symrise) | Ethylhexyl Ethylisononanoate | | | | | | | | | 2.0 | | |
| Edenor L2 SM (Cognis) | Stearic Acid, Palmitic Acid | | 24.0 | | | | | | | | | |
| Edenor K 12-18 (Cognis) | Coconut-Palmkernel Oil Fatty Acid | | 10.0 | | | | | | | | | |
| EDTA B Powder (BASF) | Tetrasodium EDTA | | | 0.2 | | | | | | | | |
| EDETA DB (BASF) | Disodium EDTA | 0.1 | | | | | 0.1 | | | | 0.1 | |
| Emulsiphos (Symrise) | Potassium Cetyl Phosphate, Hydrogenated Palm Glycerides | 1.5 | | | | | 1.5 | | | 2.0 | | |
| Ethanol 96% | Alcohol Denat. | | | | 8.0 | 5.0 | | | | | | |
| Extrapone Guarana (Symrise) | Water (Aqua), Propylene Glycol, *Paullinia Cupana* Seed Extract, Alcohol | | | | | | | | 0.5 | | | |
| Extrapone Witch Hazel Distillate colourless (Symrise) | Propylene Glycol, *Hamamelis Virginiana* (Witch Hazel) Water, Water (Aqua), *Hamamelis Virginiana* (Witch Hazel) Extract | | | | | | | 1.0 | | | 0.2 | |

TABLE 5-continued

| Raw Material Name (Manufacturer) | INCI | 4 | 5 | 6 | 7 | 8 | 9 | 10 | 11 | 12 | 13 | 14 |
|---|---|---|---|---|---|---|---|---|---|---|---|---|
| Extrapone Rosemary GW (Symrise) | Glycerin, Water (Aqua), *Rosmarinus officinalis* (Rosemary) Leaf Extract | | | | | | | | | 0.5 | | |
| Extrapone Seaweed (Symrise) | Water (Aqua), Propylene Glycol, Potassium Iodide, *Fucus Vesiculosus* Extract | | | | | | | | | 2.5 | | |
| Frescolat MGA (Symrise) | Menthone Glycerin Acetal | | 0.5 | | | | | | | | | |
| Frescolat ML cryst. (Symrise) | Menthyl Lactate | | | 0.3 | 0.5 | | | | 0.2 | | | |
| Genapol LRO liquid (Cognis) | Sodium Laureth Sulfate | | | | | | | 37.0 | | | | |
| Givobio GZN (Seppic) | Zinc Gluconate | | | | | | | | | 0.5 | | |
| Glycerol 85% | Glycerin | 3.5 | 2.3 | | | 4.7 | 4.7 | 2.0 | | 3.0 | 1.7 | |
| Hydrolite-5 (Symrise) | Pentylene Glycol | | | 5.0 | 5.0 | | | | | | 3.0 | 5.0 |
| Hydroviton 24 (Symrise) | Water, Pentylene Glycol, Glycerin, Sodium Lactate, Lactic Acid, Serine, Urea, Sorbitol, Sodium Chloride, Allantoin | | | | | | | | | 1.0 | | 1.0 |
| Isoadipate (Symrise) | Diisopropyl Adipate | 2.0 | | | | | | | | | | |
| Isodragol (Symrise) | Triisononanoin | | | | | | | | | | 3.0 | 1.0 |
| Karion F (Merck) | Sorbitol | | | | | | | 2.0 | | | | |
| Keltrol T (Danby-Chemie) | Xanthan Gum | 0.2 | | | | 0.2 | | | | | | |
| Kojic acid (Cosmetochem) | Kojic Acid | 0.5 | | | | | | | | | | |
| Lanette 16 (Cognis) | Cetyl Alcohol | 1.5 | | | | | | | | | | |
| Lanette O (Cognis) | Cetearyl Alcohol | | | | | 1.0 | | | | 3.5 | 2.0 | |
| Locron L (Cognis) | Aluminium Chlorohydrate | | | | | | | | | | | 16.0 |
| Magnesium Chloride (Merck) | Magnesium Chloride | | | | | | | 0.7 | | | | |
| Neo Heliopan 357 (Symrise) | Butyl Methoxy-dibenzoyl-methane | 2.0 | | | | 1.0 | | | | | | |
| Neo Heliopan AP (Symrise) (10% as sodium salt) | Disodium Phenyl Dibenzimidazole Tetrasulfonate | | | | | | 10.0 | | | | | |
| Neo Heliopan AV (Symrise) | Ethylhexyl Methoxy-cinnamate | 7.5 | | | | 3.0 | | | | | | |
| Neo Heliopan BB (Symrise) | Benzophenone-3 | 3.0 | | | | | | | | | | |

TABLE 5-continued

| Raw Material Name (Manufacturer) | INCI | 4 | 5 | 6 | 7 | 8 | 9 | 10 | 11 | 12 | 13 | 14 |
|---|---|---|---|---|---|---|---|---|---|---|---|---|
| Neo Heliopan Hydro (Symrise) (15% as sodium salt) | Phenylbenzimidazole Sulfonic Acid | | | | | | 6.7 | | | | | |
| Neo Heliopan HMS (Symrise) | Homosalate | 10.0 | | | | | | | | | | |
| Neo Heliopan MBC (Symrise) | 4-Methylbenzylidene Camphor | | | | | | 1.5 | | | | | |
| Neo Heliopan OS (Symrise) | Ethylhexyl Salicylate | 5.0 | | | | | 5.0 | | | | | |
| Neo-PCL Water Soluble N (Symrise) | Trideceth-9, PEG-5 Ethylhexanoate, Water (Aqua) | | | 1.0 | | | | | 1.5 | | | 2.0 |
| Neutral Oil | Caprylic/Capric Triglyceride | | 3.0 | | 5.0 | 2.0 | | | | 10.0 | | |
| Oxynex 2004 (Merck) | BHT | | | | | | 0.1 | | | | | |
| Oxynex ST Liquid (Merck) | Diethylhexyl Syringylidene Malonate) | | | | | | | | | 0.5 | | |
| PCL Liquid 100 (Symrise) | Cetearyl Ethylhexoate | | | | 4.0 | | | | | | 3.0 | |
| PCL Solid (Symrise) | Stearyl Heptanoate, Stearyl Caprylate | | | | 0.5 | | | | | | 1.0 | |
| PCL-Liquid (Symrise) | Cetearyl Ethylhexanoate, Isopropyl Myristate | | | | | | | 12.0 | | | | |
| Pemulen TR-2 (Noveon) | Acrylates/C10-30 Alkyl Acrylate Crosspolymer | | | | | 0.25 | | | | | | |
| Polymer JR 400 (Nordmann, Rassmann) | Polyquaternium-10 | | | | | | | | 0.4 | | | |
| Polyquart H 81 (Cognis) | PEG-15 Coco Polyamine | | | | | | | | | 3.0 | | |
| Potassium Hydroxide 50% Solution | Potassium Hydroxide | | | 11.0 | | | | | | | | |
| Potassium Sorbate | Potassium Sorbate | | | | | 0.1 | | | | | | |
| Propylene Glycol-1,2 99 | Propylene Glycol | | | | 5.0 | | | | | | | 3.0 |
| Retinyl Palmitate in Oil (DSM Nutrional Products) | Retinyl Palmitate | | | | | | | 0.2 | | | | |
| Sodium Ascorbyl Phosphate (EMD Chemicals) | Sodium Ascorbyl Phosphate | 1.0 | | | | | | | | | | |
| Sodium Chloride | Sodium Chloride | | | | | | | | 0.1 | 2.0 | | |
| Sodium Hydroxide 50% Solution | Sodium Hydroxide | | | 1.0 | | | | | | | | |
| Sodium Hydroxide 10% Solution | Sodium Hydroxide | 0.2 | | | 0.7 | | | | | 0.3 | 1.0 | |

TABLE 5-continued

| Raw Material Name (Manufacturer) | INCI | % | | | | | | | | | | |
|---|---|---|---|---|---|---|---|---|---|---|---|---|
| | | 4 | 5 | 6 | 7 | 8 | 9 | 10 | 11 | 12 | 13 | 14 |
| Solubilizer (Symrise) | PEG-40 Hydrogenated Castor Oil, Trideceth-9, Water (Aqua) | | | 1.5 | | | | | | | | 3.0 |
| Sun Flower Oil (Wagner) | *Helianthus Annuus* (Sunflower) Seed Oil | | | | | | 5.0 | | | | | |
| Sweet Almond Oil (Wagner) | *Prunus dulcis* | | | | | | 5.0 | | | | | |
| SymCalmin (Symrise) | Butylene Glycol, Pentylene Glycol, Hydroxyphenyl Propamidobenzoic Acid | | | | | 0.2 | | | | | 1.0 | |
| SymClariol (Symrise) | Decylene Glycol | | | | | | | | | 1.0 | | |
| SymDeo MPP (Symrise) | Dimethyl Phenyl 2-Butanol | | | | | | | | | | | 0.5 |
| Symdiol 68 (Symrise) | 1,2-Hexanediol, Caprylyl Glycerol | | | | | | | | | 1.0 | | |
| SymGlucan (ymrise) | Water (Aqua), Glycerin, Beta-Glucan | | | | | 1.0 | | | | | | |
| SymHelios (Symrise) | Benzylidene Dimethoxy-dimethylindanone | | | | | | 0.1 | | | | | |
| SymMatrix (Symrise) | Maltodextrin, *Rubus Fruticosus* (Blackberry) Leaf Extract | | | | | 0.2 | 1.0 | | | | | |
| Symrise Fragrance | Fragrance | 0.3 | 1.0 | 0.1 | 0.25 | 0.4 | 0.4 | 0.5 | 0.3 | 0.3 | 0.2 | 1.0 |
| SymVital (Symrise) | *Aloe Barbadensis* leaf juice powder, Magnesium Ascorbyl Phosphate, *Rubus Idaeus* (Raspberry) Leaf Extract | | | | 0.1 | | | | | | | |
| SymWhite 377 (Symrise) | Phenylethyl Resorcinol | 0.5 | | | | | | | | | | |
| Tamasterol (Tama Biochemicals) | Phytosterols | | | | | | | | | | 0.3 | |
| Tego Betain L7 (Degussa) | Cocamidopropyl Betaine | | | | | | | | 8.0 | | | |
| Tegosoft PC 31 (Degussa) | | | | | | | | | | | 0.3 | |
| Tegosoft TN (Degussa) | C12-15 Alkyl Benzoate | | | | | 5.0 | | | | | | |
| Triethanolamine, 99% | Triethanolamine | | | | | 0.3 | 0.5 | | | | | |
| Tocopherol Acetate (DSM Nutritional Products) | Tocopheryl Acetate | | | | | 0.5 | 3.0 | | | 0.3 | | |
| Water, demineralized | Water (Aqua) | to 100 | to 100 | to 100 | to 100 | to 100 | to 100 | to 100 | to 100 | to 100 | to 100 | to 100 |

EXAMPLES 15-24

Oral Care Products and Products for the Treatment of Sore Throat

A mixture S consisting of 99% bisabolol and 1% [6]-paradol, a mixture T consisting of 97% bisabolol and 3% [6]-paradol or a mixture R consisting of 99.5% bisabolol and 0.5% [6]-paradol were employed in Examples 15-24.

The mixtures S, T and R were each exposed in pure form to simulated sunlight to (lamp: ULTRA-VITALUX 300 W, distance UV lamp to sample: 50 cm) over a period of 24 hours. No discolouration and no chemical degradation were observed after 24 h.

EXAMPLE 15

Gel Dental Cream Having Anti-Irritant Activity

|  | I (%) | II (%) | III (%) |
|---|---|---|---|
| Na carboxymethylcellulose | 0.40 | 0.40 | 0.40 |
| Sorbitol 70%, in water | 72.00 | 72.00 | 72.00 |
| Polyethylene glycol (PEG) 1500 | 3.00 | 3.00 | 3.00 |
| Na saccharinate | 0.07 | 0.07 | 0.07 |
| Na fluoride | 0.24 | 0.24 | 0.24 |
| p-Hydroxybenzoic acid (PHB) ethyl ester | 0.15 | 0.15 | 0.15 |
| Peppermint aroma | 1.00 | 1.00 | 1.00 |
| Mixture S | 0.10 |  |  |
| Mixture T |  | 0.05 |  |
| Mixture R |  |  | 0.15 |
| Abrasive silica | 11.00 | 11.00 | 11.00 |
| Thickening silica | 6.00 | 6.00 | 6.00 |
| Sodium dodecyl sulfate (SDS) | 1.40 | 1.40 | 1.40 |
| Dist. water | to 100.00 | to 100.00 | to 100.00 |

EXAMPLE 16

Dental Cream Against Plaque Having Anti-Irritant Activity

|  | I (%) | II (%) | III (%) |
|---|---|---|---|
| Carrageenan | 0.90 | 0.90 | 0.90 |
| Glycerin | 15.00 | 15.00 | 15.00 |
| Sorbitol 70%, in water | 25.00 | 25.00 | 25.00 |
| PEG 1000 | 3.00 | 3.00 | 3.00 |
| Na fluoride | 0.24 | 0.24 | 0.24 |
| Tetrapotassium diphosphate | 4.50 | 4.50 | 4.50 |
| Tetrasodium diphosphate | 1.50 | 1.50 | 1.50 |
| Na saccharinate | 0.40 | 0.40 | 0.40 |
| Precipitated silica | 20.00 | 20.00 | 20.00 |
| Titanium dioxide | 1.00 | 1.00 | 1.00 |
| PHB methyl ester | 0.10 | 0.10 | 0.10 |
| Spearmint aroma | 1.10 | 1.10 | 1.10 |
| Mixture S |  |  | 0.20 |
| Mixture T | 0.05 |  |  |
| Mixture R |  | 0.10 |  |
| Sodium dodecyl sulfate | 1.30 | 1.30 | 1.30 |
| Dist. water | to 100.00 | to 100.00 | to 100.00 |

EXAMPLE 17

Dental Cream Against Sensitive Teeth Having Anti-Irritant Activity

|  | I (%) | II (%) | III (%) |
|---|---|---|---|
| Na carboxymethylcellulose | 0.70 | 0.70 | 0.70 |
| Xanthan gum | 0.50 | 0.50 | 0.50 |
| Glycerin | 15.00 | 15.00 | 15.00 |
| Sorbitol 70%, in water | 12.00 | 12.00 | 12.00 |
| K nitrate | 5.00 | 5.00 | 5.00 |
| Na monofluorophosphate | 0.80 | 0.80 | 0.80 |
| PHB methyl ester | 0.15 | 0.15 | 0.15 |
| PHB propyl ester | 0.05 | 0.05 | 0.05 |
| Na saccharinate | 0.20 | 0.20 | 0.20 |
| *Eucalyptus*/menthol aroma | 1.00 | 1.00 | 1.00 |
| Mixture S | 0.03 |  |  |
| Mixture T |  |  | 0.15 |
| Mixture R |  | 0.07 |  |
| Ca carbonate | 35.00 | 35.00 | 35.00 |
| Silicon dioxide | 1.00 | 1.00 | 1.00 |
| Sodium dodecyl sulfate (SDS) | 1.50 | 1.50 | 1.50 |
| Dist. water | to 100.00 | to 100.00 | to 100.00 |

EXAMPLE 18

Ready-to-Use Mouthwash with Fluoride

|  | I (%) | II (%) | III (%) |
|---|---|---|---|
| Ethanol | 7.00 | 7.00 | 7.00 |
| Glycerin | 12.00 | 12.00 | 12.00 |
| Na fluoride | 0.05 | 0.05 | 0.05 |
| Pluronic F-127 ® (BASF, surface-active substance) | 1.40 | 1.40 | 1.40 |
| Na phosphate buffer pH 7.0 | 1.10 | 1.10 | 1.10 |
| Sorbic acid | 0.20 | 0.20 | 0.20 |
| Na saccharinate | 0.10 | 0.10 | 0.10 |
| Cinnamon/menthol aroma | 0.15 | 0.15 | 0.15 |
| Mixture S |  |  | 0.20 |
| Mixture T |  | 0.10 |  |
| Mixture R | 0.05 |  |  |
| Dyestuff | 0.01 | 0.01 | 0.01 |
| Dist. water | to 100.00 | to 100.00 | to 100.00 |

EXAMPLE 19

Mouthwash Concentrate Having Anti-Irritant Activity

|  | I (%) | II (%) | III (%) |
|---|---|---|---|
| Ethanol, 95% strength | 80.00 | 80.00 | 80.00 |
| Na cyclamate | 0.15 | 0.15 | 0.15 |
| *Eucalyptus*/wintergreen aroma | 3.50 | 3.50 | 3.50 |
| Dyestuff | 0.01 | 0.01 | 0.01 |
| Mixture S |  |  | 3.00 |
| Mixture T | — | 1.00 | — |
| Mixture R | 0.50 |  |  |
| Dist. water | to 100.00 | to 100.00 | to 100.00 |

EXAMPLE 20

Chewing Gum with Anti-Irritant Activity

|  | I (%) | II (%) | III (%) |
|---|---|---|---|
| Chewing gum base | 21.00 | 21.00 | 21.00 |
| Glucose syrup | 16.50 | 16.50 | 16.50 |
| Glycerin | 0.50 | 0.50 | 0.50 |
| Powdered sugar | 60.45 | 60.36 | 60.27 |
| Spearmint aroma | 1.50 | 1.50 | 1.50 |
| Mixture S | 0.05 | | |
| Mixture T | | | 0.25 |
| Mixture R | | 0.10 | |

EXAMPLE 21

Sugar-Free Chewing Gum with Anti-Irritant Activity

|  | I (%) | II (%) | III (%) |
|---|---|---|---|
| Chewing gum base | 30.00 | 30.00 | 30.00 |
| Sorbitol, powder | ad 100 | ad 100 | ad 100 |
| Palatinite | 9.50 | 9.50 | 9.50 |
| Xylitol | 2.00 | 2.00 | 2.00 |
| Mannitol | 3.00 | 3.00 | 3.00 |
| Aspartame | 0.10 | 0.10 | 0.10 |
| Acesulfame K | 0.10 | 0.10 | 0.10 |
| Emulgum/emulsifier | 0.30 | 0.30 | 0.30 |
| Sorbitol 70%, in water | 14.00 | 14.00 | 14.00 |
| Glycerin | 1.00 | 1.00 | 1.00 |
| Cinnamon/menthol aroma | 1.50 | 1.50 | 1.50 |
| Mixture S | | | 0.20 |
| Mixture T | | 0.10 | |
| Mixture R | 0.05 | | |

EXAMPLE 22

Gelatine Capsules with Anti-Irritant Activity for Direct Consumption

|  | I (%) | II (%) | III (%) |
|---|---|---|---|
| Gelatine shell: | | | |
| Glycerin | 2.014 | 2.014 | 2.014 |
| Gelatine 240 Bloom | 7.91 | 7.91 | 7.91 |
| Sucralose | 0.065 | 0.065 | 0.065 |
| Allura Red | 0.006 | 0.006 | 0.006 |
| Brilliant Blue | 0.005 | 0.005 | 0.005 |
| Core composition: | | | |
| Plant oil triglyceride | 82.00 | 74.00 | 60.00 |
| Aroma B [#] | 7.85 | 15.50 | 28.50 |
| Mixture S | 0.10 | | 0.50 |
| Mixture T | | 0.25 | |

[#] Aroma B here had the following composition (data in each case in wt. %):
0.1% neotame powder, 0.05% aspartame, 29.3% peppermint oil *arvensis*, 29.3% peppermint *piperita* oil Willamette, 2.97% sucralose, 2.28% triacetin, 5.4% diethyl tartrate, 12.1% peppermint oil yakima, 0.7% ethanol, 3.36% 2-hydroxyethyl menthyl carbonate, 3.0% 2-hydroxypropyl menthyl carbonate, 0.27% vanillin, 5.5% D-limonene, 5.67% L-menthyl acetate.

The gelatine capsule, which is suitable for direct consumption, had a diameter of 5 mm, to and the weight ratio of core material to shell material was 90:10. The capsules opened in the mouth within less than 10 seconds and dissolved completely within less than 50 seconds.

EXAMPLE 23

Fruit Gums with Anti-Irritant Activity

|  | I (%) | II (%) |
|---|---|---|
| Water | to 100 | to 100 |
| Saccharose | 34.50 | 34.50 |
| Glucose syrup, DE 40 | 31.89 | 31.89 |
| Iso Syrup C* Tru Sweet 01750 (Cerestar GmbH) | 1.50 | 1.50 |
| Gelatine 240 Bloom | 8.20 | 8.20 |
| Yellow and red colouring | 0.01 | 0.01 |
| Citric acid | 0.20 | 0.20 |
| Mixture S | | 0.20 |
| Mixture T | 0.05 | |

EXAMPLE 24

Hard Caramel (Hard Boiled Candy)

|  | I (%) | II (%) |
|---|---|---|
| Sugar (sucrose) | to 100 | to 100 |
| Maize syrup (corn syrup), contains glucose and fructose | 41.00 | 41.00 |
| Maltose | 3.00 | 3.00 |
| Palm kernel oil | 0.90 | 0.90 |
| Citric acid | 0.30 | 0.30 |
| *Ginseng* extract | — | 0.40 |
| Blue dyestuff | 0.01 | 0.01 |
| Mixture S | | 0.10 |
| Mixture R | 0.30 | |
| Honey | — | 1.50 |
| Honey flavour | — | 0.30 |

The sugar, corn syrup and maltose were dissolved in water and the solution was boiled and placed under a vacuum. The remaining ingredients were then sucked into the boiled sugar mass and the mixture was homogenized at the boiling temperature. After cooling, hard caramels were stamped out of the resulting mass.

The hard caramels showed a residual water content of about 2.5%.

The invention claimed is:

1. A formulation having a skin irritation-reducing action comprising an irritation-reducing amount of [6]-paradol and bisabolol, wherein the weight ratio of [6]-paradol to bisabolol is in the range of from 1:100000 to 1:10, wherein the formulation is free of [6]-gingerol, provided that the amount of [6]-paradol is at least 10 ppm, based on the total weight of the formulation, and that the skin irritation-reducing action of the combination of [6]-paradol and bisabolol is increased synergistically relative to the skin irritation-reducing action of [6]-paradol and bisabolol individually.

2. The formulation according to claim 1, wherein
the total amount of [6]-paradol is in the range of from 0.001 to 10 wt. %, and/or
the total amount of bisabolol is in the range of from 99.999 to 90 wt. %, based on the total weight of the formulation.

3. The formulation according to claim 1, wherein the formulation is a cosmetic formulation.

4. The cosmetic formulation according to claim 3, wherein the total amount of [6]-paradol and bisabolol is in the range of from 0.001 to 5 wt. %, based on the total weight of the formulation.

5. A medicament comprising a formulation according to claim 1.

6. A cosmetic product comprising a formulation according to claim 1.

7. A pharmaceutical product for prophylaxis and/or treatment of skin irritation comprising a formulation according to claim 1.

8. A formulation according to claim 1, further comprising
one or more organic UVA filter substances and/or
one or more organic UVB filter substances and/or
one or more organic UVA and UVB filter substances and/or
one or more inorganic UV filter substances.

9. A formulation according to claim 1, further comprising
one or more antioxidants and/or
one or more cooling agents and/or
one or more antimicrobials and/or
one or more hair growth inhibitors.

10. A formulation according to claim 1, further comprising a substance having skin-irritating action, wherein the total amount of bisabolol and [6]-paradol in the formulation is sufficient to reduce, eliminate or suppress the skin irritating action of the substance.

11. A process for the preparation of a formulation according to claim 1 comprising combining [6]-paradol and bisabolol in amounts sufficient to synergistically increase the skin irritation-reducing action of [6]-paradol and bisabolol.

12. A method for the treatment of skin irritation comprising applying a formulation according to claim 1 to non-irritated skin.

13. A kit comprising (i) a formulation according to claim 1 and (ii) one or more substances having a skin-irritating action, wherein (i) and (ii) are spatially separated from one another.

14. The formulation according to claim 1, wherein the weight ratio of [6]-paradol to bisabolol is in the range of 1:10000 to 1:20.

15. The formulation according to claim 1, wherein the weight ratio of [6]-paradol to bisabolol is in the range of 1:1000 to 1:33.

16. The formulation according to claim 1, wherein the formulation is free of gingerols and shogaols.

17. The formulation according to claim 1, wherein the formulation is free of gingerols, shogaols, gingerdiols, dehydrogingerdiones and zingerone.

* * * * *